(12) United States Patent
Yamasaki et al.

(10) Patent No.: US 9,327,123 B2
(45) Date of Patent: May 3, 2016

(54) ENDOVASCULAR NERVE MONITORING DEVICES AND ASSOCIATED SYSTEMS AND METHODS

(71) Applicant: Medtronic Ardian Luxembourg S.a.r.l., Luxembourg (LU)

(72) Inventors: Dwayne S. Yamasaki, Jacksonville, FL (US); Bryan Courtney, Jacksonville, FL (US); Wenjeng Li, Jacksonville, FL (US); Kevin Mauch, Santa Rosa, CA (US); Kevin McFarlin, Jacksonville, FL (US); Gabriel Brennan, Ballybrit (IE); David Gannon, Ballybrit (IE); David Hobbins, Ballybrit (IE); Brian Kelly, Ballybrit (IE); Stephen Nash, Ballybrit (IE); Matthew Bonner, Ballybrit (IE); Sean Ward, Ballybrit (IE)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 13/670,452

(22) Filed: Nov. 6, 2012

(65) Prior Publication Data

US 2013/0131743 A1    May 23, 2013

Related U.S. Application Data

(60) Provisional application No. 61/556,776, filed on Nov. 7, 2011.

(51) Int. Cl.
*A61B 18/02* (2006.01)
*A61N 1/36* (2006.01)
(Continued)

(52) U.S. Cl.
CPC .......... *A61N 1/36125* (2013.01); *A61B 5/4035* (2013.01); *A61B 5/4041* (2013.01);
(Continued)

(58) Field of Classification Search
CPC ..... A61N 1/05; A61N 1/0507; A61N 1/0509; A61N 1/0551; A61N 1/0558; A61N 1/306; A61N 1/36; A61N 1/36007
USPC .......................... 607/2, 40, 44, 62, 116, 133
See application file for complete search history.

(56) References Cited

U.S. PATENT DOCUMENTS 4,602,624 A    7/1986 Naples et al.
4,649,936 A    3/1987 Ungar et al.
(Continued)

FOREIGN PATENT DOCUMENTS

EP    1169976    1/2002
EP    2316371    5/2011
(Continued)

OTHER PUBLICATIONS

Allen, E.V., Sympathectomy for essential hypertension, Circulation, 1952, 6:131-140.
(Continued)

*Primary Examiner* — George Evanisko

(57) ABSTRACT

Endovascular nerve monitoring devices and associated systems and methods are disclosed herein. A nerve monitoring system configured in accordance with a particular embodiment of the present technology can include a shaft having a proximal portion and a distal portion and a nerve monitoring assembly at the distal portion. The shaft is configured to locate the distal portion intravascularly at a treatment site. The nerve monitoring assembly can include a bipolar stimulation electrode array and a bipolar recording electrode array disposed distal to the bipolar stimulation electrode assembly.

10 Claims, 17 Drawing Sheets

(51) Int. Cl.
    *A61B 5/00*     (2006.01)
    *A61N 1/05*     (2006.01)
    *A61B 18/00*     (2006.01)
    *A61B 18/14*     (2006.01)
    *A61B 5/20*     (2006.01)

(52) U.S. Cl.
CPC ............. *A61B5/4833* (2013.01); *A61B 5/6853* (2013.01); *A61B 5/6856* (2013.01); *A61B 18/1492* (2013.01); *A61N 1/3605* (2013.01); *A61N 1/36017* (2013.01); *A61N 1/36171* (2013.01); *A61N 1/36175* (2013.01); *A61B 5/201* (2013.01); *A61B 5/4893* (2013.01); *A61B 2018/0022* (2013.01); *A61B 2018/00404* (2013.01); *A61B 2018/00434* (2013.01); *A61B 2018/00511* (2013.01); *A61B 2018/00654* (2013.01); *A61B 2018/00839* (2013.01); *A61B 2018/0212* (2013.01); *A61B 2018/1407* (2013.01); *A61B 2018/1435* (2013.01); *A61N 1/0558* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,149,574 B2 | 12/2006 | Yun et al. |
| 7,160,296 B2 | 1/2007 | Pearson et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 1,002,882 A1 | 2/2011 | LAU et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,702,619 B2 | 4/2014 | Wang |
| 8,768,470 B2 | 7/2014 | Deem et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel et al. |
| 9,014,821 B2 | 4/2015 | Wang |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0265015 A1 | 11/2006 | Demarais et al. |
| 2006/0271111 A1 | 11/2006 | Demarais et al. |
| 2007/0066957 A1 | 3/2007 | Demarais et al. |
| 2007/0083239 A1 | 4/2007 | Demarais et al. |
| 2007/0129720 A1 | 6/2007 | Demarais et al. |
| 2007/0265687 A1 | 11/2007 | Deem et al. |
| 2008/0119907 A1 | 5/2008 | Stahmann |

(56) References Cited

U.S. PATENT DOCUMENTS

| | | |
|---|---|---|
| 2008/0319513 A1 | 12/2008 | Pu et al. |
| 2009/0036948 A1 | 2/2009 | Levin et al. |
| 2009/0076409 A1 | 3/2009 | Wu et al. |
| 2010/0010567 A1 | 1/2010 | Deem et al. |
| 2010/0022876 A1 | 1/2010 | Shih |
| 2010/0114244 A1 | 5/2010 | Manda et al. |
| 2010/0137860 A1 | 6/2010 | Demarais et al. |
| 2010/0137952 A1 | 6/2010 | Demarais et al. |
| 2010/0174271 A1 | 7/2010 | Kassab |
| 2010/0191112 A1 | 7/2010 | Demarais et al. |
| 2010/0222851 A1* | 9/2010 | Deem et al. ............. 607/72 |
| 2010/0222854 A1 | 9/2010 | Demarais et al. |
| 2011/0112400 A1 | 5/2011 | Emery et al. |
| 2011/0270120 A1 | 11/2011 | Mcfarlin et al. |
| 2011/0306851 A1* | 12/2011 | Wang ..................... 600/301 |
| 2012/0029504 A1 | 2/2012 | Afonso et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0143097 A1 | 6/2012 | Pike, Jr. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0265198 A1* | 10/2012 | Crow et al. ............. 606/41 |
| 2012/0290053 A1* | 11/2012 | Zhang et al. ............ 607/116 |
| 2012/0296232 A1* | 11/2012 | Ng ........................ 600/554 |
| 2012/0296329 A1 | 11/2012 | Ng |
| 2013/0085489 A1* | 4/2013 | Fain et al. .............. 606/34 |
| 2013/0116737 A1 | 5/2013 | Edwards et al. |
| 2013/0123778 A1 | 5/2013 | Richardson et al. |
| 2013/0165764 A1 | 6/2013 | Scheuermann et al. |
| 2013/0172878 A1 | 7/2013 | Smith |
| 2013/0218029 A1 | 8/2013 | Cholette et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | NISHII |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0112329 A1 | 4/2015 | Ng |
| 2015/0223877 A1 | 8/2015 | Behar et al. |

FOREIGN PATENT DOCUMENTS

| | | |
|---|---|---|
| EP | 2594193 | 5/2013 |
| EP | 2613704 | 7/2013 |
| EP | 2747691 | 7/2014 |
| EP | 2797535 | 11/2014 |
| WO | WO-2014091328 | 7/1989 |
| WO | WO-9407446 | 4/1994 |
| WO | WO-9525472 | 9/1995 |
| WO | WO-9531142 | 11/1995 |
| WO | WO-9736548 | 10/1997 |
| WO | WO-9900060 | 1/1999 |
| WO | WO-0122897 | 4/2001 |
| WO | WO-0170114 | 9/2001 |
| WO | WO-03022167 | 3/2003 |
| WO | WO-03/082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO-2010078175 | 7/2010 |
| WO | WO-2012033974 | 3/2012 |
| WO | WO-2012158864 | 11/2012 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014091401 | 6/2014 |
| WO | WO-2014149550 | 9/2014 |
| WO | WO-2014149552 | 9/2014 |
| WO | WO-2014149553 | 9/2014 |
| WO | WO-2014149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014158708 | 10/2014 |
| WO | WO-2014158713 | 10/2014 |
| WO | WO-2014163990 | 10/2014 |
| WO | WO-2014179768 | 11/2014 |
| WO | WO-2014182946 | 11/2014 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney- Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, The American Physiological Society 1983, pp. F1-F14.

Krum, Henry et al., "Catheter-Based Renal Sympathetic Denervation for Resistant Hypertension: a Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

(56) References Cited

OTHER PUBLICATIONS

Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 The American Physiological Society, pp. 2034-2039.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Intery Cardiac Electrophysiol, 2:285-292 (1998).
Gelfand, M., et al., "Treatment of renal failure and hypertension." U.S. Appl. No. 60/442,970, 2003.
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Intery Radiol, 12: 862-868 (2001).
Hanson, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrhythmias." Progr Cardiovasc Dis, 41:481-498 (1999).
Medical-Dictionary.com, Definition of "Animal Model," http://medical-dictionary.com (search "Animal Model"), 2005.
Medtronic, Inc., Annual Report (Form 10-K) (Jun. 28, 2011).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Peet, M., "Hypertension and its Surgical Treatment by bilateral supradiaphragmatic splanchnicectomy" Am J Surgery (1948) pp. 48-68.
Renal Denervation (RDN), Symplicity Rdn System Common Q&A (2011), http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: a comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Weinstock, M., et al., "Renal denervation prevents sodium retention and hypertension in salt sensitive rabbits with genetic baroreflex impairment." Clinical Science, 90:287-293 (1996).
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A.., "Endovascular Skills—Guidewires, Catheters, Arteriography, Balloon Angioplasty, Stents", pp. 70-71, 101 and 188-190 (1998).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006).
Mount Sinai School of Medicine clinical trial for Impact of Renal Sympathetic Denervation of Chronic Hypertension, Mar. 2013, http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.

(56) References Cited

OTHER PUBLICATIONS

Opposition to European Patent No. EP2037840, Granted Dec. 7, 2011, Date of Opposition Sep. 7, 2012, 25 pages.
Oz, Mehmet, Pressure Relief, TIME, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20 :484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Chinushi et al., "Blood Pressure and Autonomic Responses to Electrical Stimulation of the Renal Arterial Nerves Before and After Ablation of the Renal Artery." Hypertension, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
European Search Report for European Application No. 13159256, Date Mailed: Oct. 17, 2013, 6 pages.
International Search Report and Written Opinion for International App. No. PCT/IB2012/003055, Date Mailed: Oct. 28, 2013, 16 pages.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life- Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinicunveils-top-10-medical-innovations-for-2012.aspx>.
"Does renal denervation represent a new treatment option for resistant hypertension?" Interventional News, Aug. 3, 2010, 2 pages. <http://www.cxyascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N. V., 2013, Europe, 3 pages.
"Neurotech Reports Announces Winners of Gold Electrode Awards." Neurotech business report, 2009. 1 page. <http://www.neurotechreports.com/pp./goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul lntegr Comp Physiol, vol. 274, 1998, 7 pages.
Bengel, Frank, "Serial Assessment of Sympathetic Reinnervation After Orthotopic Heart Transplantation: A longitudinal Study Using Pet and C-11 Hydroxyephedrine." Circulation, vol. 99, 1999, 7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines__article&force-id=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.

(56) References Cited

OTHER PUBLICATIONS

Linz, Dominik et al., "Renal denervation suppresses ventricular arrhythmias during acute ventricular ischemia in pigs." Heart Rhythm, vol. 0, No. 0, 2013, 6 pages.

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Millard, F. C., et al, "Renal Embolization for ablation of function in renal failure and hypertension." Postgraduate Medical Journal, 65, 729-734 (1989).

Ormiston, John et al., "First-in-human use of the OneShotTM renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated Esh position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stouffer, G. A. et al., "Catheter-based renal denervation in the treatment of resistant hypertension." Journal of Molecular and Cellular Cardiology, vol. 62, 2013, 6 pages.

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Beale et al., "Minimally Invasive Treatment for Varicose Veins: a Review of Endovenous Laser Treatment and Radiofrequency Ablation". Lower Extremity Wounds 3(4), 2004, 10 pp.

Clinical Plus "Kidney Functional Unit" Dec. 20, 2012, http://clinicalplus.wordpress.com/2012/12/20/kidney-functional.unit 4 pages.

Kopp, U. C., "Neural Control of Renal Function." San Rafael (CA): Morgan & Claypool Life Sciences; 2011, Chapter 7, Neuroanatomy, 2 pages.

Beale et al., "Minimally Invasive Treatment for Varicose Veins: A Review of Endovenous Laser Treatment and Radiofrequency Ablation". Lower Extremity Wounds 3(4), 2004, 10 pages.

Schneider, Peter A., "Endovascular Skills—Guidewire and Catheter Skills for Endovascular Surgery," Second Edition Revised and Expanded, 10 pages, (2003).

Stella, A., et al., "Effects of reversable renal denervation on haemodynamic and excretory functions on the ipsilateral and contralateral kidney in the cat." Hypertension, 4: 181-188 (1986).

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Pieper et al., "Design and Implementation of a New Computerized System for Intraoperative Cardiac Mapping." Journal of Applied Physiology, 1991, vol. 71, No. 4, pp. 1529-1539.

Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 5416.

U.S. Appl. No. 60/852,787, filed Oct. 18, 2006, 112 pages.

* cited by examiner

*Arterial Vasculature*

*Venous Vasculature*

ENDOVASCULAR NERVE MONITORING DEVICES AND ASSOCIATED SYSTEMS AND METHODS

CROSS-REFERENCE TO RELATED APPLICATION(S)

This application claims the benefit of and priority to U.S. Provisional Patent Application No. 61/556,776, filed Nov. 7, 2011, which is incorporated herein by reference in its entirety.

TECHNICAL FIELD

The present technology relates generally to nerve monitoring devices and associated systems and methods. In particular, several embodiments are directed to endovascular renal nerve monitoring devices and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation or cryotherapeutic cooling) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

Figure 1:
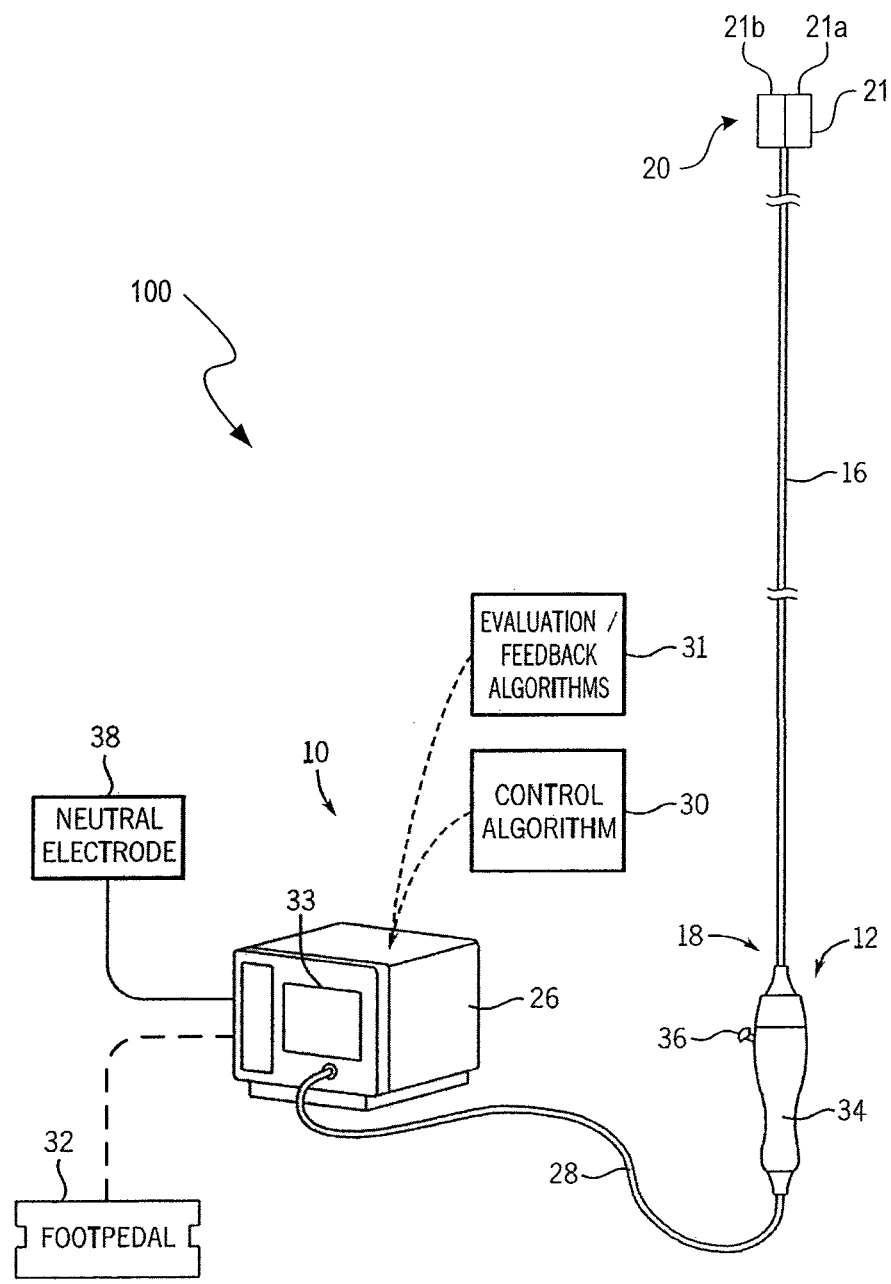
FIG. 1 illustrates a neuromodulation system configured in accordance with an embodiment of the present technology.

The present technology is directed to apparatuses, systems, and methods for intraoperatively monitoring nerve activity to determine the effects of electrically-induced and/or thermally-induced neuromodulation (i.e., rendering neural fibers inert or inactive or otherwise completely or partially reduced in function). Specific details of several embodiments of the technology are described below with reference to FIGS. 1-15. Although many of the embodiments are described below with respect to devices, systems, and methods for endovascularly monitoring renal nerve activity, other applications (e.g., monitoring nerves located elsewhere proximate to the vasculature) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-15.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation.

Various techniques can be used to partially or completely incapacitate neural pathways, such as those innervating the kidney. The purposeful application of energy (e.g., electrical energy, thermal energy) to tissue can induce one or more desired thermal heating effects on localized regions of the renal artery and adjacent regions of the renal plexus, which lay intimately within or adjacent to the adventitia of the renal artery. The purposeful application of the thermal heating and cooling effects can achieve neuromodulation along all or a portion of the renal plexus.

II. Selected Embodiments of Neuromodulation Systems

FIG. 1 illustrates a neuromodulation system 10 ("system 10") configured in accordance with an embodiment of the present technology. The system 10 includes an intravascular treatment device 12 operably coupled to an energy source or console 26 (e.g., a RF energy generator, a cryotherapy console). In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a therapeutic section 21 (shown schematically) at the distal portion 20 of the shaft 16. The therapeutic section 21 can include a neuromodulation assembly 21a and/or a nerve monitoring assembly 21b configured to be delivered endovascularly to a treatment site within the vasculature (e.g., a renal artery). The neuromodulation assembly 21a (shown schematically) can include, for example, one or more energy delivery elements (e.g., electrodes) configured to provide RF or other forms of energy, a cooling assembly configured to provide cryotherapeutic cooling, and/or other features configured to deliver therapeutically-effective neuromodulation energy to the treatment site. The nerve monitoring assembly 21b (shown schematically) can include electrodes configured to stimulate nerves proximate the treatment site and/or record the resultant nerve activity.

The therapeutic section 21 can be configured in a delivery state (e.g., a low profile arrangement) to facilitate delivery (e.g., insertion), removal and, in certain embodiments, repositioning of the therapeutic section 21 at the treatment site. Upon delivery to the treatment site, the therapeutic section 21 can be moved or transformed to a deployed state (e.g., an expanded arrangement) for delivering energy at the treatment site and providing therapeutically-effective electrically-induced and/or thermally-induced renal neuromodulation. In some embodiments, the therapeutic section 21 may be placed or transformed into the deployed state via remote actuation, e.g., via an actuator 36, such as a knob, pin, or lever carried by the handle 34. In other embodiments, however, the therapeutic section 21 may be transformed between the delivery and deployed states using other suitable mechanisms or techniques. As discussed in greater detail below, the neuromodulation assembly 21a can be integrated with the nerve monitoring assembly 21b and can provide feedback of nerve activity to verify that the neuromodulation assembly 21a provided therapeutically-effective neuromodulation. In other embodiments, the nerve monitoring assembly 21b and the neuromodulation assembly 21a can be separate devices (e.g., each connected to its own catheter shaft) such that the nerve monitoring assembly 21b can be delivered to the treatment site independently of the neuromodulation assembly 21a for nerve monitoring before, during and/or after neuromodulation.

The proximal end of the therapeutic section 21 is carried by or affixed to the distal portion 20 of the elongated shaft 16. A distal end of the therapeutic section 21 may terminate with, for example, an atraumatic rounded tip or cap. Alternatively, the distal end of the therapeutic section 21 may be configured to engage another element of the system 10 or treatment device 12. For example, the distal end of the therapeutic section 21 may define a passageway for engaging a guide wire (not shown) for delivery of the treatment device using over-the-wire ("OTW") or rapid exchange ("RX") techniques.

The energy source or console 26 may be configured to generate a selected form and magnitude of energy for delivery to the treatment site via the therapeutic section 21. For example, the energy source 26 can include a generator configured to provide RF and/or other forms of energy to the therapeutic section 21. In other embodiments, the energy source 26 can be configured as a cryogenic console configured to deliver a refrigerant to the therapeutic section 21. In further embodiments, the energy source 26 can deliver other forms of therapeutically-effective neuromodulation to the therapeutic section 21 (e.g., ultrasound energy, high intensity focused ultrasound ("HIFU"), microwave energy, optical energy, direct heat, chemical (drugs or other agents)). A control mechanism, such as foot pedal 32, may be connected (e.g., pneumatically connected or electrically connected) to the console to allow the operator to initiate, terminate and, optionally, adjust various operational characteristics of the energy generator, including, but not limited to, power delivery. The system 10 may also include a remote control device (not shown) that can be positioned in a sterile field and operably coupled to the therapeutic section 21. The remote control device is configured to allow for selective activation of the therapeutic section 21. In other embodiments, the remote control device may be built into the handle assembly 34. The energy source 26 can be configured to deliver the treatment energy via an automated control algorithm 30 and/or under the control of the clinician. In addition, the energy source 26 may include one or more evaluation or feedback algorithms 31 to provide feedback to the clinician before, during, and/or after therapy.

The energy source 26 can further include processing circuitry, such as a microprocessor, and a display 33 (e.g., a monitor). The processing circuitry may be configured to execute stored instructions relating to the control algorithm 30. For example, the energy source 26 may be configured to communicate with the treatment device 12 (e.g., via the cable 28) to control the neuromodulation assembly 21a and/or to send signals to or receive signals from the nerve monitoring assembly 21b. The display 33 may be configured to provide indications of power levels or sensor data, such as audio, visual or other indications, or may be configured to communicate the information to another device. For example, the console 26 may also be configured to be operably coupled to a catheter lab screen or system for displaying treatment information, such as nerve activity before and after treatment.

Figure 2:
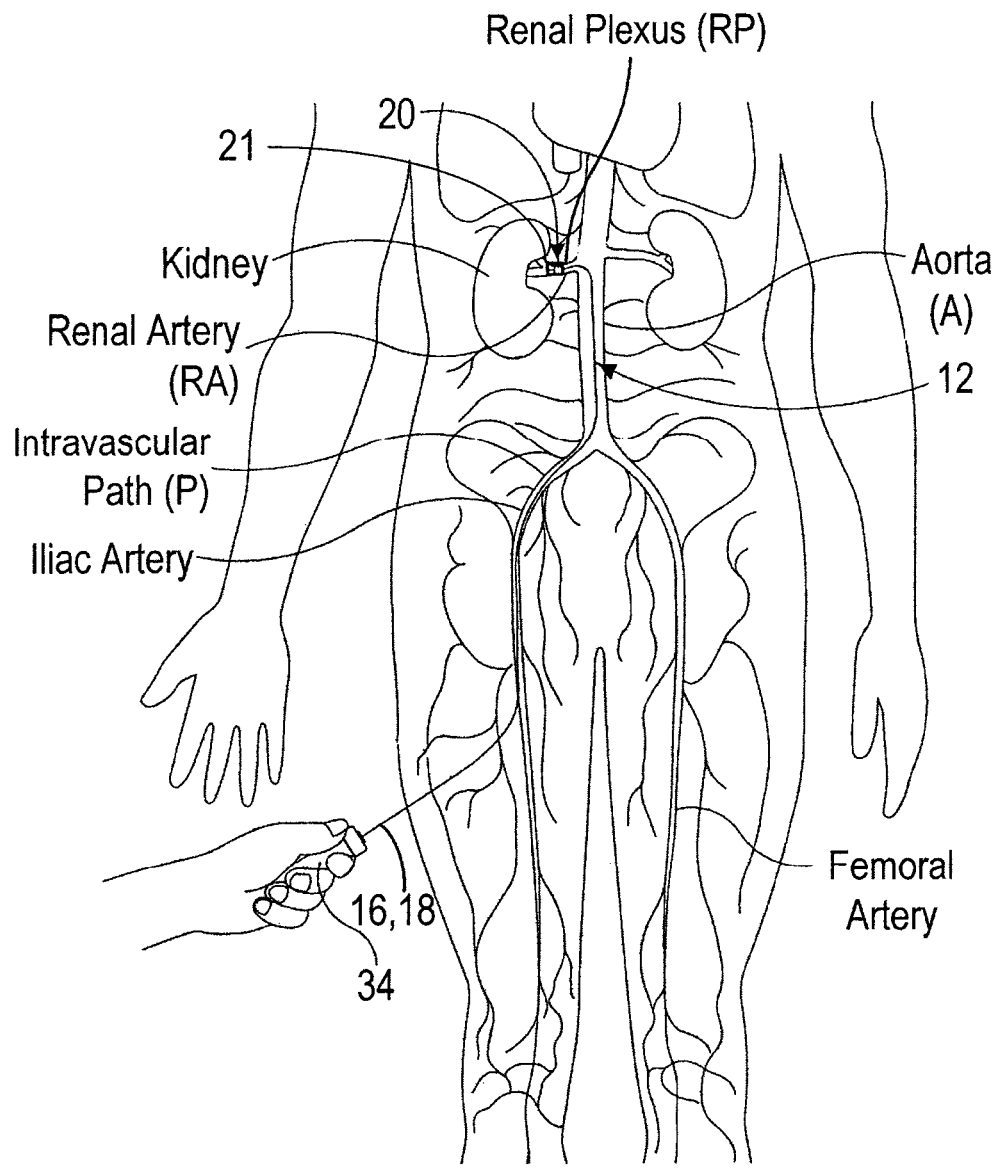
FIG. 2 illustrates modulating renal nerves with a neuromodulation system in accordance with an embodiment of the present technology.

FIG. 2 illustrates modulating renal nerves with an embodiment of the system 10. The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, a clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12 itself.

After the therapeutic section 21 is adequately positioned in the renal artery RA, it can be radially expanded or otherwise deployed using the handle 34 or other suitable means until the neuromodulation assembly 21a (FIG. 1) is positioned at its target site and the nerve monitoring assembly 21b (FIG. 1) is in stable contact with the inner wall of the renal artery RA. The purposeful application of energy from the neuromodulation assembly 21b is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. Before, during, and/or after the energy application, the nerve monitoring assembly may stimulate and record nerve activity across the wall of the renal artery to determine whether the treatment has effectuated sufficient neuromodulation.

III. Nerve Monitoring Devices and Systems

Figure 3A:
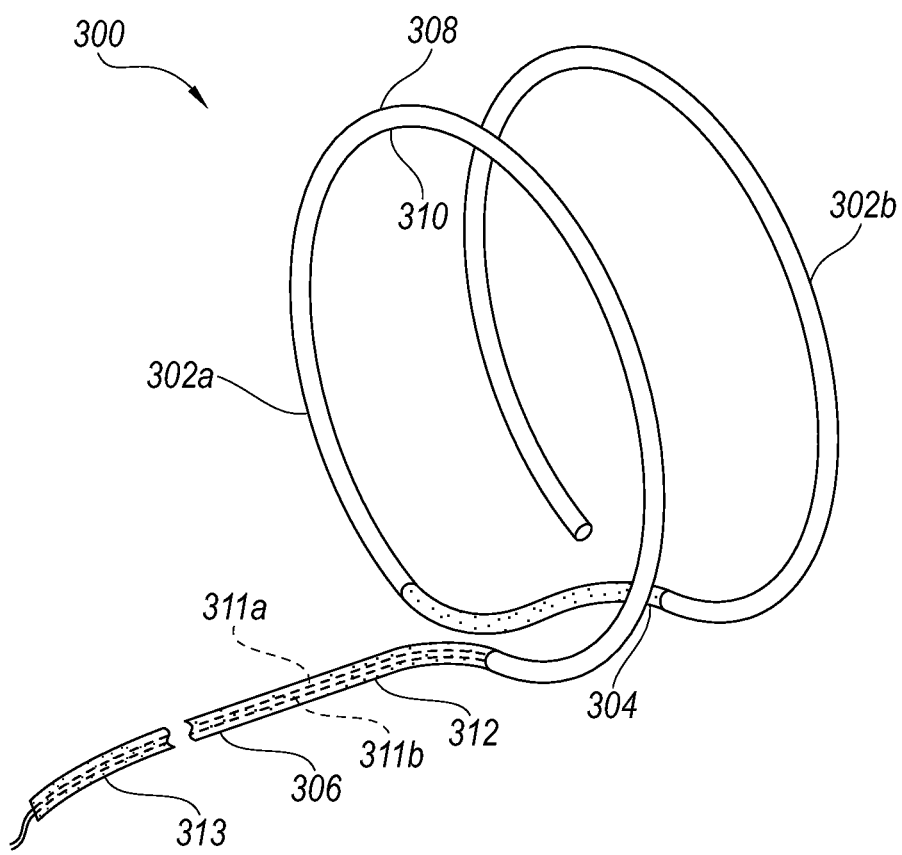
FIG. 3A is an enlarged isometric view of an electrode assembly configured in accordance with an embodiment of the present technology.

FIG. 3A is an enlarged isometric view of an electrode array or assembly 300 configured in accordance with an embodiment of the present technology. The electrode assembly 300 can be part of a nerve monitoring assembly (e.g., the nerve monitoring assembly 21b of the treatment device 12 described above with reference to FIGS. 1 and 2) that provides stimulation to neural fibers and/or records nerve activity. As shown in FIG. 3A, the electrode assembly 300 can include a first loop electrode or conductor 302a and a second loop electrode or conductor 302b (referred to collectively as loop electrodes 302) electrically isolated from the first loop electrode 302a and positioned at a distal portion 312 of an elongated catheter shaft 306. In the illustrated embodiment, the two loop electrodes 302 form a generally circular shape. However, the term "loop electrode" as used herein should be construed broadly to include electrodes 302 having other shapes configured to contact at least a portion of the interior wall of a vessel. In various embodiments, the first loop electrode 302a can be an anode, the other loop electrode 302 can be a cathode, and an insulated portion 304 can electrically isolate the anode and cathode loop electrodes 302 from one another and space the loop electrodes 302 laterally apart from one another. For example, the distal end of the first loop electrode 302a and the proximal end of the second loop electrode 302b can terminate at or within a portion of the insulating portion 304, and the insulating portion 304 can space the loop electrodes 302 approximately 3 mm to approximately 5 mm apart from one another. In other embodiments, the loop electrodes 302 can be spaced closer together or further apart. In various embodiments, the separation between the loop electrodes 302 (e.g., provided by the insulating portion 304) can be selected to enhance the signal to noise ratio for recording nerve activity (e.g., delta fibers and/or C-fibers). For example, the first and second loop electrodes 302a and 302b can be spaced about 5 mm apart from one another for recording action potentials from delta fibers, and may be positioned further apart from one another for recording C-fibers.

When the first and second loop electrodes 302a and 302b are configured as an anode and a cathode, the electrode assembly 300 can deliver bipolar stimulation to nerves proximate a target site in a vessel (e.g., renal nerves proximate the renal artery) or provide bipolar recording of nerve activity proximate the target site. For example, a nerve monitoring device configured in accordance with one embodiment of the present technology can include two electrode assemblies 300: a first electrode assembly configured to stimulate nerves and a second electrode assembly spaced apart from the first electrode assembly along the vasculature and configured to measure the action potential of the nerves resulting from the stimuli of the first electrode assembly. Action potential is the electrical activity developed in a nerve cell during activity (e.g., induced by a stimulus from the first electrode assembly).

The loop electrodes 302 can have an outer diameter at least equal to an inner diameter of a target vessel and, in some cases, larger (e.g., 1.5 times larger) than the inner diameter of the target vessel. For example, in embodiments configured to fit within renal arteries that have inner diameters of approximately 3 mm to approximately 10 mm, the loop electrodes 302 can have an outer diameter of 3 mm to 15 mm (e.g., 6 mm, 8 mm, 10 mm, etc.). In other embodiments, the loop electrodes 302 can be sized to contact the inner wall of other vessels (e.g., the aorta).

Each loop electrode 302 can be made from a separate shape memory wire that defines the electrode 302. The shape memory wire allows the loop electrodes 302 to be positioned in a low profile, delivery state during intravascular delivery to the target vessel and open transverse to the longitudinal axis of the target vessel to an expanded or deployed state (shown in FIG. 3A). For example, the loop electrodes 302 can be made from nitinol wires that can self-expand to a predefined shape upon delivery at the target vessel. In various embodiments, the shape memory material can be coated (e.g., sputter coated) with gold, platinum, platinum iridium, and/or other suitable materials. The coating can be selected to substantially optimize the impedance of the electrode assembly 300 and/or enhance the signal-to-noise ratio recorded by the electrode assembly 300. In other embodiments, the loop electrodes 302 can be made from other suitable materials (e.g., platinum, gold, platinum iridium, stainless steel, aluminum, etc.). The wire thickness of each loop electrode 302 can be sized such that the loop electrode 302 is stable enough to maintain its shape during nerve monitoring, yet flexible enough to allow for intravascular delivery in a low profile arrangement to a peripheral vessel (e.g., a renal blood vessel). In one embodiment, for example the wire of each loop electrode 302 can have a thickness of approximately 0.006 inch (0.152 mm). In other embodiments, the electrode wire can be larger (e.g., 0.012 inch (0.305 mm)) or smaller.

Each loop electrode 302 of the electrode assembly 300 can have an exposed abluminal surface 308 (e.g., an outer surface proximate the vessel wall during nerve monitoring) to deliver and/or receive electrical signals to neural fibers proximate to a target vessel and an insulated adluminal or luminal surface 310 (e.g., an inner surface facing away from the vessel wall and toward the lumen formed by the target vessel) to reduce the likelihood that blood flowing through the target vessel will short circuit the loop electrodes 302. The luminal surface 310 may be insulated using a coating with a high dielectric constant, strong adhesive properties to prevent it from rubbing off during delivery, biocompatible properties suitable for intravascular use, and/or other suitable characteristics.

As mentioned previously, the total exposed abluminal surface 308 of the electrode assembly 300 can be selected to enhance the signal-to-noise ratio of the electrode assembly 300. In various embodiments, for example, the electrode assembly 300 can be configured to have an exposed abluminal surface area of about 4-20 mm$^2$ (0.006-0.031 in$^2$) depending upon the outer diameter of the loop electrodes 302 and the wire diameter of each loop electrode 302. For example, an electrode assembly made of two loop electrodes 302 having a wire diameter of 0.012 inch (0.305 mm) and an outer diameter of 8 mm may have a total exposed surface area of approximately 12 mm$^2$. In other embodiments, however, the loop electrodes 302 can be made from wire having different thicknesses and/or the loop electrodes 302 can have smaller or larger outer diameters.

The electrode assembly 300 can be delivered intravascularly to a treatment site before and/or after neuromodulation. The distal portion 312 of the shaft 306 (e.g., having a length of approximately 10 cm to 25 cm in length) can be made from various flexible polymeric materials, such as a polyethylene block amide copolymer (e.g., PEBAX®, available from Arkema of France), high-density polyethylene (HDPE), nylon, polyimide, and/or other suitable materials, to facilitate navigation through tortuous vasculature. The distal portion 312 can also include braid reinforcement comprised of polymeric materials to improve column strength, torque, and reduce kinking. A proximal portion 313 of the shaft 306 (e.g., the proximal portion 18 of the shaft 16 of FIGS. 1 and 2) can be more stiff than the distal portion 312, and can therefore transmit force to track the shaft 306 through the vasculature to the target site (e.g., proximate the renal arteries). The proximal portion 313 can be made from PEBAX®, HDPE, low-density polyethylene (LDPE), nylon, polyimide, nylon, nitinol, a stainless steel hypotube, and/or other suitable materials. In various embodiments, the distal end portion of the electrode assembly 300 can include an atraumatic tip when the electrode assembly 300 is in the delivery state to reduce trauma to vessel walls as the electrode assembly 300 advances through the vasculature and deploys at the target site. This atraumatic tip material can be made from various soft materials, such as PEBAX®, LDPE, other polymers, and/or other suitable materials. The distal tip can also include a radiopaque tip marker (electrically isolated from the loop electrodes 302) to provide visualization of the distal tip under fluoroscopy.

Signal wires 311 (referred to individually as a first signal wire 311a and a second signal wire 311b; shown in broken lines) can be operatively coupled to the electrode assembly 300 to drive nerve stimulation, record nerve activity, and/or otherwise provide a signal to the loop electrodes 302. The signal wires 311, for example, can be welded, soldered, crimped, and/or otherwise connected to the shaft 306. A distal portion of the first signal wire 311a can be operably coupled to the first loop electrode 302a, and a distal portion of the second signal wire 311b can be operably coupled to the second loop electrode 302b. The signal wires 311 can extend through the shaft 306 to a proximal end of the shaft where the signal wires 311 can be operatively connected to a signal processing console (e.g., the console 26 of FIG. 1) suitable for nerve stimulation. In various embodiments, for example, one or more electrode assemblies 300 can be operatively coupled to a NIM-Response Nerve Integrity Monitor ("NIM") made available by Medtronic Xomed of Jacksonville, Fla., which provides intraoperative nerve monitoring capabilities using visual and/or audible indications of nerve activity.

Figure 3B:
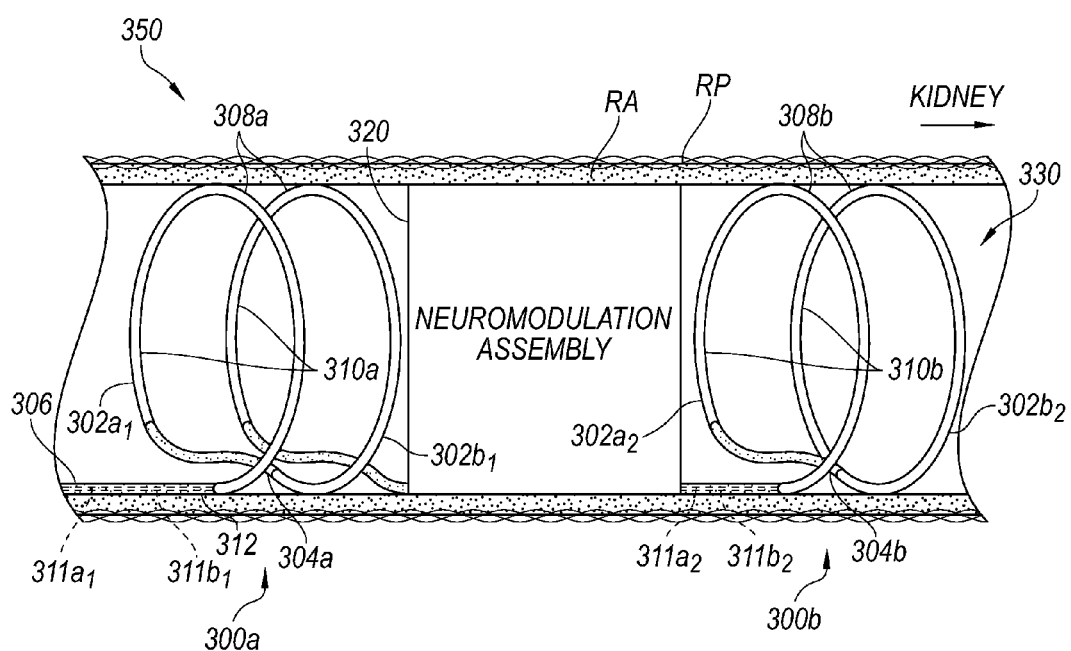
FIG. 3B is an enlarged partially schematic view of a distal portion of a treatment device within a renal artery in accordance with an embodiment of the present technology.

FIG. 3B is an enlarged partially schematic side view of a distal portion of a treatment device 350 positioned in a renal artery RA and configured in accordance with an embodiment of the present technology. The treatment device 350 can include features generally similar to the features of the treatment device 12 described above with reference to FIGS. 1 and 2 and be part of a neuromodulation system including features generally similar to those of the neuromodulation system 10 of FIGS. 1 and 2. For example, the distal portion of the treatment device 350 includes a neuromodulation assembly 320 (shown schematically) and a nerve monitoring assembly 330. The neuromodulation assembly 320 can be virtually any suitable energy delivery device configured to cause therapeutically-effective nerve modulation, such as a cryotherapeutic catheter or a single or multi-electrode neuromodulation device. In the illustrated embodiment, the neuromodulation assembly 320 is operatively coupled to and positioned between two electrode assemblies 300 (identified individually as a first electrode assembly 300a and a second electrode assembly 300b) described above with reference to FIG. 3A, which together define the nerve monitoring assembly 330. In other embodiments, the neuromodulation assembly 320 and the nerve monitoring assembly 330 may be stand-alone devices that can be delivered independently to a target site (e.g., within the renal artery). For example, in some embodiments the second electrode assembly 300b, the neuromodulation assembly 320 and the first electrode assembly 300a are coupled to separate catheter shafts (e.g., the shaft 16 of FIG. 1) and delivered sequentially to the target site to provide a configuration similar to that shown in FIG. 3B. In still other embodiments, the first and second electrode assemblies 300a and 300b can be integrally coupled to one another and delivered to the target site before and/or after neuromodulation.

The nerve monitoring assembly 330 can be configured to stimulate the renal plexus RP proximally with the first electrode assembly 300a and record nerve activity distally with the second electrode assembly 300b. The first electrode assembly 300a can be positioned inward from the ostium of the renal artery RA (e.g., about 1 cm (0.393 inch) where the renal nerves may be positioned about 6 mm (2.362 inches) away from the renal artery RA) such that the renal nerves are close enough to the surface of the renal artery RA to receive stimulation from the first electrode assembly 300a. The second electrode assembly 300b can be positioned distal to the first electrode assembly 300a, closer to the bifurcation of the renal artery RA (e.g., where the renal nerves can be about 2 mm (0.787 inch) from the surface of the renal artery RA) such that the renal nerves are close enough to the second electrode assembly 300b for it to record nerve activity (i.e., action potentials). Accordingly, the second electrode assembly 300b can be configured to have an impedance that is low enough record nerve activity from at least 2 mm (0.787 inch) outside the renal artery RA or other vessel wall. In other embodiments, the second electrode assembly 300b can be configured to record nerve activity from nerves spaced more than 2 mm (0.787 inch) outside a vessel wall and/or closer to a vessel wall. In further embodiments, the second electrode assembly 300b can be configured to provide stimulation and the first electrode assembly 300a can be configured to record the resultant nerve activity.

The first and second electrode assemblies 300a and 300b can be spaced far enough apart from one another such that the signal artifact associated with the bipolar stimulation from the first electrode assembly 300a, which is less than that which would be produced by monopolar stimulation, does not substantially engulf or otherwise interfere with the signal being recorded at the second electrode assembly 300b. The magnitude of the signal artifact at the second electrode assembly 300b depends at least in part on the conduction velocity of the nerve fibers and the spacing between the stimulus and recording electrodes. C-fibers and delta-fibers, such as those found in nerves, have relatively low conduction velocities (e.g., no more than 2 m/s for C-fibers and about 3-13 m/s for delta fibers). As such, when the second electrode assembly 300b is configured to record renal nerve activity, the second electrode assembly 300b can be positioned at least 5 mm (e.g., 10 mm, 15 mm, etc.) laterally apart from the first electrode assembly 300a along the axis of the renal artery RA to reduce the signal artifact recorded by the second electrode assembly 300b. In other embodiments, the first and second electrode assemblies 300a and 300b can be spaced different distances apart from one another (e.g., about 5-30 mm apart, 10-20 mm apart) along the axis of the renal artery RA and/or other vessel. In further embodiments, at least one of the electrode assemblies 300 can be positioned outside the renal artery RA. For example, in some embodiments the second electrode assembly 300b can be positioned in the renal artery RA to record nerve activity, and the first electrode assembly 300a can be positioned elsewhere within the vasculature (e.g., in the aorta, at the ostium of the renal artery RA, etc.) that can deliver a stimulus to renal nerves. In still other embodiments, the first electrode assembly 300a can be configured to stimulate nerves from a location outside the human body (e.g., at the brain stem), and the second electrode assembly 300b can be configured to record the resultant nerve activity at a site within or proximate to the renal artery RA. In additional embodiments, the electrode assemblies 300 can be configured to be placed at other suitable locations for stimulating and recording nerve activity.

In various embodiments, the first electrode assembly 300a can be configured to provide biphasic and bipolar stimulation. The second loop electrode $302b_1$ (i.e., the electrode closest to the recording/second electrode assembly 302b) can be a cathode and the first loop electrode $302a_1$ an anode. In some embodiments, the first electrode assembly 300a can stimulate the renal nerves with an electrical current having a magnitude of 20 mA to 30 mA using an electrical generator at the proximal portion 313 (FIG. 3A) of the shaft 306 (e.g., a NIM and/or other suitable console). For example, a generator can be configured such that the first electrode assembly 300a delivers about 20 mA, 20 Hz wave signals at a pulse width of about 100-1,000 μs. In other embodiments, the first electrode assembly 300a can deliver signals having different intensities, higher or lower frequencies, different shapes and/or other pulse widths. The exposed surface area of the first electrode assembly 300a can be selected (e.g., based on the loop diameter, wire diameter, and any insulating coating) such that the current density is high enough to stimulate proximate nerve fibers without substantially disturbing the integrity of the arterial wall. In other embodiments, the first electrode assembly 300a can deliver more or less stimulation.

The second electrode assembly 300b can be configured to provide bipolar recording of nerve activity resulting from the stimulation induced by the first electrode assembly 300a. As such, the first loop electrode $302a_2$ can be one of an anode or a cathode, and the second loop electrode $302b_2$ can be the other of the anode or the cathode. The second electrode assembly 300b can pick up the relatively small action potentials (e.g., action potentials of 0.5 μV to 1.5 μV) associated with renal nerve activity, and can be sensitive to relatively small signals (e.g., 0.1 μV) to differentiate nerve stimulation from noise. In order to pick up the small action potentials and differentiate the nerve activity from noise (e.g., from the signal artifact, action potentials of proximate muscle fibers, etc.), the second electrode assembly 300b can be configured to record a plurality of samples that can be averaged (e.g., using a NIM or other suitable console). In one embodiment, for example, the second electrode assembly 300b can average 160 samples within 12 seconds to identify the nerve activity. In other embodiments, more or less samples can be averaged to identify the nerve activity.

As shown in FIG. 3B, the first and second electrode assemblies 300a and 300b and the neuromodulation assembly 320 can be attached to the distal portion 312 of the same shaft 306 such that the nerve monitoring assembly 330 and the neuromodulation assembly 320 can be delivered as a unit to the target site. In one embodiment, for example, the neuromodulation assembly 320 includes a neuromodulation loop electrode that is connected between the first and second electrode assemblies 300a and 300b. The first and second electrode assemblies 300a and 300b can be stiffer than the neuromodulation loop electrode such that the electrode assemblies 300 stay substantially planar in the renal artery RA and provide adequate contact with the arterial walls to stimulate the nerves and record the resultant nerve activity. The neuromodulation loop electrode may be more flexible, allowing it to be pulled into a helix or corkscrew configuration during deployment at the target site while the first and second electrode assemblies 300a and 300b stay anchored against the renal artery RA due to self-expansion. In other embodiments, each electrode assembly 300 and/or the neuromodulation assembly 320 can be attached to separate shafts and delivered independently to the target site.

In various embodiments, the nerve monitoring assembly 330 (in conjunction with or independent of the neuromodulation assembly 320) can be delivered intravascularly to the renal artery RA or other peripheral vessel via a delivery sheath (not shown). The delivery sheath can extend along the length of the shaft 306, and can be made from PEBAX®, nylon, HDPE, LDPE, polyimide, and/or other suitable materials for navigating the vasculature. The delivery sheath can cover the electrode assemblies 300 such that they are positioned in a low profile, delivery state suitable for navigation through the vasculature. At the renal artery RA, the delivery sheath can be moved relative to the electrode assemblies 300 (e.g., the sheath can be retracted or the electrode assemblies 300 can be advanced) to expose the electrode assemblies 300 from the sheath 300. This allows the electrode assemblies 300 to deploy (e.g., self-expand) into an expanded state where the abluminal surfaces 308 of the loop electrodes 302 contact the arterial wall. In other embodiments, the delivery sheath is not integrated to the nerve monitoring assembly 330, and advanced over a guide wire to the treatment site via a guide catheter. In this embodiment, the delivery sheath can be made from a soft, flexible material that allows it to navigate tortuous vessels. Once the delivery sheath is at the target site in the renal artery RA, the electrode assemblies 300 can be positioned in a proximal opening of the delivery sheath and advanced distally to the treatment site where they can be deployed to the expanded state by moving the delivery sheath and the electrode assemblies 300 relative to one another.

As shown in FIG. 3B, in the expanded state, the loop electrodes 302 of the first and second electrode assemblies 300a and 300b are sized to press against or otherwise contact the interior wall of the renal artery RA. For example, the loop electrodes 302 can have an outer diameter of 8 mm (0.314 inch) in the expanded state such that the abluminal surfaces 308 of the loop electrodes 302 adequately contact the inner wall of a typical renal artery RA (e.g., typically having an inner diameter of 4-8 mm (0.157-0.314 inch)). In other embodiments, the outer diameter of the loop electrodes 302 can be larger or smaller to appropriately contact an adjacent vessel wall. The nerve monitoring system 330 can first monitor nerve activity in real time before neuromodulation by delivering an electrical current (e.g., 20-30 mA) proximal to a treatment site via the first electrode assembly 300a and recording the resultant nerve activity at the second electrode assembly 300b. The first and second loop electrodes $302a_1$ and $302b_1$ of the first electrode assembly 300a can be operably coupled to first and second signal wires $311a_1$ and $311b_1$, respectively, to provide bipolar stimulation, and the first and second loop electrodes $302a_2$ and $302b_2$ of the second electrode assembly 300b can be operably coupled to two separate signal wires $311a_2$ and $311b_2$, respectively, to provide bipolar recording, or vice versa. Since the abluminal surface 308 of the loop electrodes 302 are fully exposed, the first electrode assembly 300a can deliver stimulation to nerves positioned around the full circumference of the renal artery RA. The exposed abluminal surface 308 also allows the second electrode assembly 300b to capture nerve activity regardless of nerve orientation around the circumference of the renal artery RA. The insulated luminal surface 310 of the loop electrodes 302 insulates the electrode assemblies 300 from blood flowing through the renal artery RA to avoid a short circuit between the electrode loops 302. The recording can be visualized using a console (e.g., a NIM) coupled to the proximal portion (FIG. 3A) of the shaft 306.

The neuromodulation assembly 320 can then apply an energy field to the target site to cause electrically-induced and/or thermally-induced partial or full denervation of the kidney (e.g., using electrodes or cryotherapeutic devices). The nerve monitoring assembly 330 can again stimulate and record the nerve activity to determine whether sufficient neuromodulation occurred. If the nerve monitoring assembly 330 indicates the presence of a higher level of nerve activity than desired, the neuromodulation assembly 320 can again apply the energy field to effectuate neuromodulation. This process of supplying a current, recording the resultant nerve activity, and applying neuromodulation to the treatment site can be repeated until the desired nerve lesion is achieved. In some embodiments, such as when the neuromodulation assembly 320 uses cryotherapeutic cooling to denervate the kidney, the nerve monitoring assembly 330 can also record nerve activity during denervation. Once nerve monitoring at the treatment site is complete, the delivery sheath can again be advanced over the electrode assemblies 300 and/or the electrode assemblies 300 can be retracted into the delivery sheath, thereby moving the electrode assemblies 300 back into the delivery state for removal from the patient.

In further embodiments, the nerve monitoring assembly 330 can be operatively coupled to the neuromodulation assembly 320 such that nerve monitoring and neuromodulation can run automatically as part of a preset program. In other embodiments, the nerve monitoring assembly 330 is not positioned around the neuromodulation assembly 320, but instead delivered to the treatment site separately before and/or after neuromodulation by the neuromodulation assembly 320.

In various embodiments, the first and second electrode assemblies 300a and 300b can be delivered after neuromodulation to confirm the desired neuromodulation has occurred. For example, the two electrode assemblies 300 can be delivered proximate the treatment site as separate components or as an integrated unit to a vessel (e.g., the renal artery) during the neuromodulation procedure a short time after neuromodulation occurs (e.g., 5 minutes after neuromodulation). In other embodiments, the electrode assemblies 300 can be used to monitor nerve activity during a separate procedure following the neuromodulation procedure (e.g., 1, 2 or 3 days after the neuromodulation procedure).

Figure 4A:
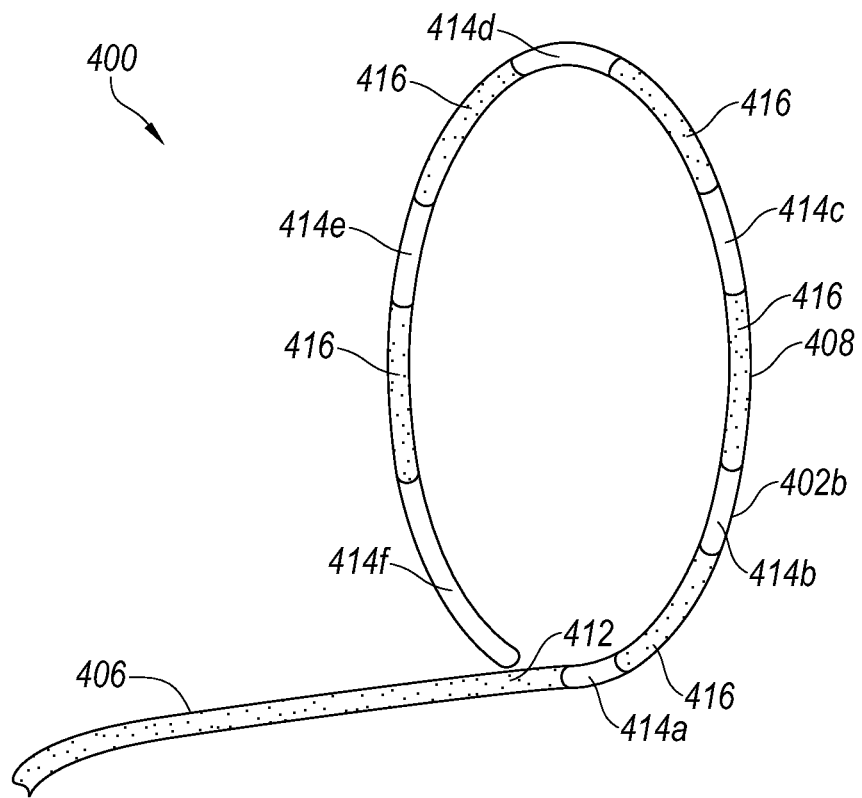
FIG. 4A is an enlarged isometric view of an electrode assembly configured in accordance with another embodiment of the present technology.

FIG. 4A is an enlarged isometric view of an electrode assembly 400 configured in accordance with another embodiment of the present technology. The electrode assembly 400 can include features generally similar to the electrode assembly 300 described above with reference to FIGS. 3A and 3B. For example, the electrode assembly 400 includes a loop 402

(e.g., a nitinol wire) at a distal portion 412 of an elongated shaft 406 that is configured to provide bipolar, biphasic nerve stimulation and/or record the resultant nerve activity. However, the electrode assembly 400 shown in FIG. 4A includes a plurality of electrodes 414 (identified individually as first through sixth electrodes 414a-f, respectively) positioned around the circumference of the loop 402 spaced apart and electrically insulated from one another by insulating sections 416. The electrodes 414 can be made from stainless steel, gold, platinum, platinum iridium, aluminum, nitinol, and/or other suitable materials, and the insulation sections 416 can be made from a suitable dielectric material (e.g., a high-k dielectric with strong adhesive properties). The electrodes 414 can be substantially coplanar with an outer surface of the insulating sections 416 and/or the shaft 406, or may project beyond the insulating sections 416 by a distance (e.g., about 0.2-0.5 mm). In various embodiments, for example, the electrodes 414 can extend a radial distance from the adjacent insulating portions 416 and include a smoothed edge (e.g., a beveled edge) to reduce denuding of the adjacent arterial wall. The coplanar or projecting electrodes 414 can facilitate contact with the arterial wall to enhance stimulation and/or recording. In other embodiments, one or more of the electrodes 414 may be recessed from the insulating portions 416.

In the illustrated embodiment, the multi-electrode loop 402 includes six electrodes 414a-f, which may be suitable for loops having outer diameters of approximately 8 mm. In other embodiments, however, the loop 402 can include more or less electrodes 414 (e.g., four to eight electrodes 414) depending at least in part on the outer diameter of the loop 402. Each of the electrodes 414 can be designated as a cathode, anode, or inactive by a nerve monitoring console (e.g., a NIM and/or other suitable console) operably coupled to the multi-electrode loop 402 via signal wires extending through the shaft 406. For example, the electrodes 414 can alternate as anodes and cathodes around the circumference of the loop 402 (e.g., the first, third and fifth electrodes 414a, 414c and 414e can be anodes and the second, fourth and sixth electrodes 414b, 414d and 414f can be cathodes) such that the single loop 402 can provide bipolar stimulation or recording. Similar to the loop electrodes 302 described above, a luminal surface 410 of the multi-electrode loop 402 can also be insulated to inhibit short circuits across the electrodes 414 (e.g., via blood or other conductive pathways), while an abluminal surface 408 can remain exposed to allow the electrodes 414 to contact a vessel wall (e.g., the renal artery).

In various embodiments, the electrode assembly 400 can include two loops 402 spaced laterally apart from one another (e.g., similar to the dual loop electrode assembly 300 shown in FIG. 3A). This arrangement allows all the electrodes 414 on one multi-electrode loop 402 to be configured as anodes, while all the electrodes 414 on the other multi-electrode loop 402 can be configured as cathodes. Much like the loop electrodes 302 shown in FIG. 3A, the double multi-electrode loop configuration can increase the surface area with which the electrode assembly 400 can stimulate and/or capture nerve activity, and can therefore enhance nerve monitoring.

Figure 4B:
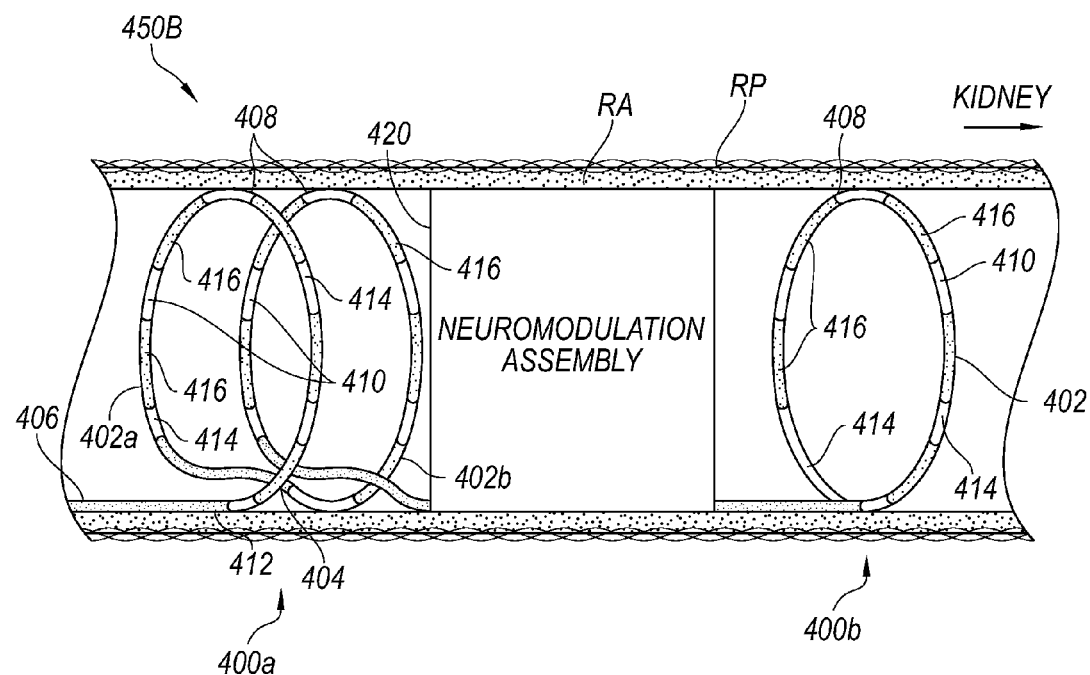
FIG. 4B is an enlarged partially schematic view of a distal portion of a treatment device within a renal artery in accordance with another embodiment of the present technology.

FIG. 4B is an enlarged partially schematic side view of a distal portion of a treatment device 450B within a renal artery RA configured in accordance with another embodiment of the present technology. The treatment device 450B includes features generally similar to the features of the treatment device 350 described above with reference to FIG. 3B. For example, the treatment device 450B includes a neuromodulation assembly 420 positioned between and optionally operably coupled to a first electrode assembly 400a and a second electrode assembly 400b. The first electrode assembly 400a includes two multi-electrode loops 402 (identified individually as a first multi-electrode loop 402a and a second multi-electrode loop 402b). In various embodiments, all the electrodes 414 of the first multi-electrode loop 402a can be anodes, and all the electrodes 414 of the second multi-electrode loop 402b can be cathodes such that the first electrode assembly 400a can provide bipolar nerve stimulation. In the embodiment illustrated in FIG. 4B, the second electrode assembly 400b includes one multi-electrode loop 402 having both anodes and cathodes spaced around the circumference to provide bipolar recording of nerve activity. In other embodiments, the second electrode assembly 400b can include two multi-electrode loops 402 and designate one as a cathode and the other as an anode. In further embodiments, the first electrode assembly 400a and/or the second electrode assembly 400b can include two bare loop electrodes 302 as shown in FIG. 3B. In still further embodiments, the electrode assemblies 400 can be configured to provide monopolar nerve stimulation or recording.

Figure 4C:
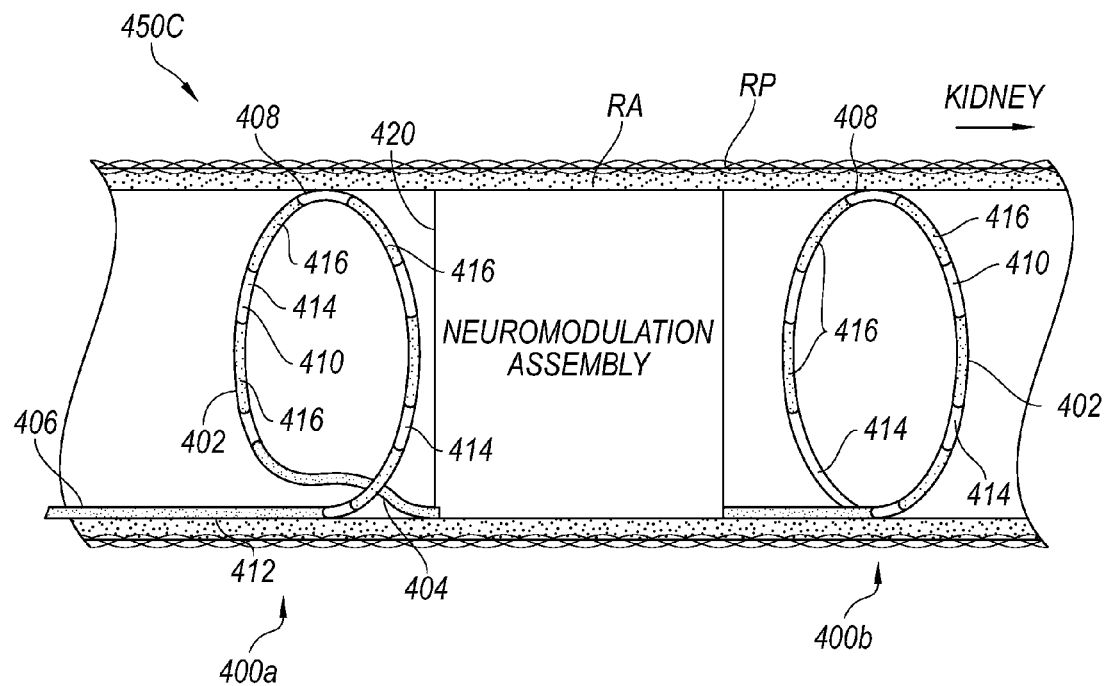
FIG. 4C is an enlarged partially schematic view of a distal portion of a treatment device within a renal artery in accordance with yet another embodiment of the present technology.

FIG. 4C is an enlarged partially schematic side view of a distal portion of a treatment device 450C within a renal artery RA in accordance with yet another embodiment of the present technology. The treatment device 450C includes features generally similar to the features of the treatment device 450B described above with reference to FIG. 4B. For example, the treatment device 450C includes the neuromodulation assembly 420 positioned between the first electrode assembly 400a and the second electrode assembly 400b. In the embodiment illustrated in FIG. 4C, however, the first electrode assembly 400a includes only one multi-electrode loop 402 such that the loop 402 includes both anodes and cathodes to provide the desired bipolar stimulation.

Figure 5:
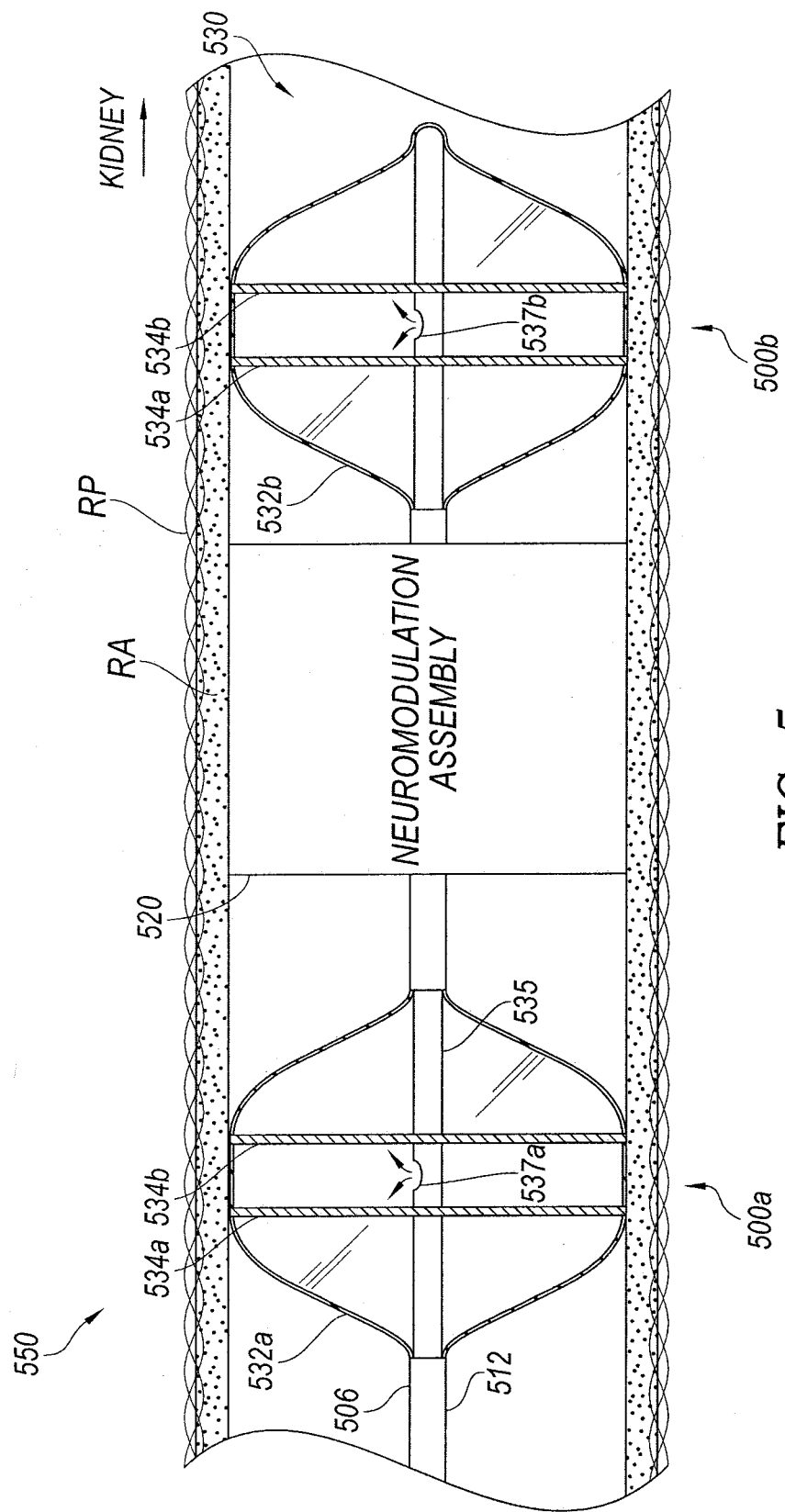
FIG. 5 is an enlarged partially schematic side view of a distal portion of a treatment device within a renal artery in accordance with a further embodiment of the present technology.

FIG. 5 is an enlarged partially schematic side view of a distal portion of a treatment device 550 within a renal artery RA in accordance with a further embodiment of the present technology. The treatment device 550 includes features generally similar to the features of the treatment devices described above with reference to FIGS. 3B, 4B and 4C. The treatment device 550, for example, includes a neuromodulation assembly 520 (shown schematically) and a nerve monitoring assembly 530 at a distal portion 512 of a shaft 506. The neuromodulation assembly 520 is positioned between a first electrode assembly 500a that provides bipolar nerve stimulation and a second electrode 500b that provides bipolar recording of nerve activity (collectively referred to as electrode assemblies 500). In the illustrated embodiment, each electrode assembly 500 includes a balloon 532 (identified individually as a first balloon 532a and a second balloon 532b) having one or more conductive portions 534 (identified individually as a first conductive portion 534a and a second conductive portion 534b) that serve as electrodes. The conductive portions 534 can be made from a conductive ink that is sufficiently flexible to allow the balloons 532 to fold into a guide catheter (not shown) during delivery and removal of the treatment device 550. In other embodiments, the conductive portions 534 can be made from other suitable materials that attach to the balloons 532, such as platinum iridium wires.

In the embodiment illustrated in FIG. 5, each balloon 532 includes two spaced apart conductive portions 534 around at least a portion of the circumference of the balloon 532 such that the conductive portions 534 can contact the inner arterial wall of the renal artery RA when the balloons 532 are inflated (e.g., as shown in FIG. 5). The balloons 532 can be inflated by flowing gas (e.g., air) or liquid (e.g., saline solution) into the balloons 532 through one or more openings 537 (referred to individually as a first opening 537a and a second opening 537b) in a tube 535 that is coupled to a fluid source (not shown) at a proximal end portion and extends through the balloons 532 at a distal end portion. Similar to the multi-loop electrode assemblies described above, the two conductive portions 534 of each balloon 532 can be designated as an anode and as a cathode to provide bipolar nerve stimulation and recording. In other embodiments, at least one of the electrode assemblies 500 can include a dual balloon, and each balloon can include one conductive portion 534 such that the nerve monitoring assembly 530 includes three or four balloons.

In various embodiments, the neuromodulation assembly 520 can be omitted. As such, the electrode assemblies 500 can be intravascularly delivered to the treatment site (e.g., at the renal artery RA) to record nerve activity before neuromodulation. The electrode assemblies 500 can then be removed from the target site to allow the neuromodulation assembly 520 to be delivered. After neuromodulation, the electrode assemblies 500 can be delivered back to the target site to record the nerve activity. If a sufficient nerve lesion has not been formed, the neuromodulation assembly 520 can again be delivered to the treatment site to deliver an energy field to ablate or otherwise modulate the nerves. The neuromodulation assembly 520 can then be removed from the treatment site to allow the electrode assemblies 500 to be delivered and monitor the resultant nerve activity. This process can be repeated until a sufficient nerve lesion is formed at the target site.

Figure 6:
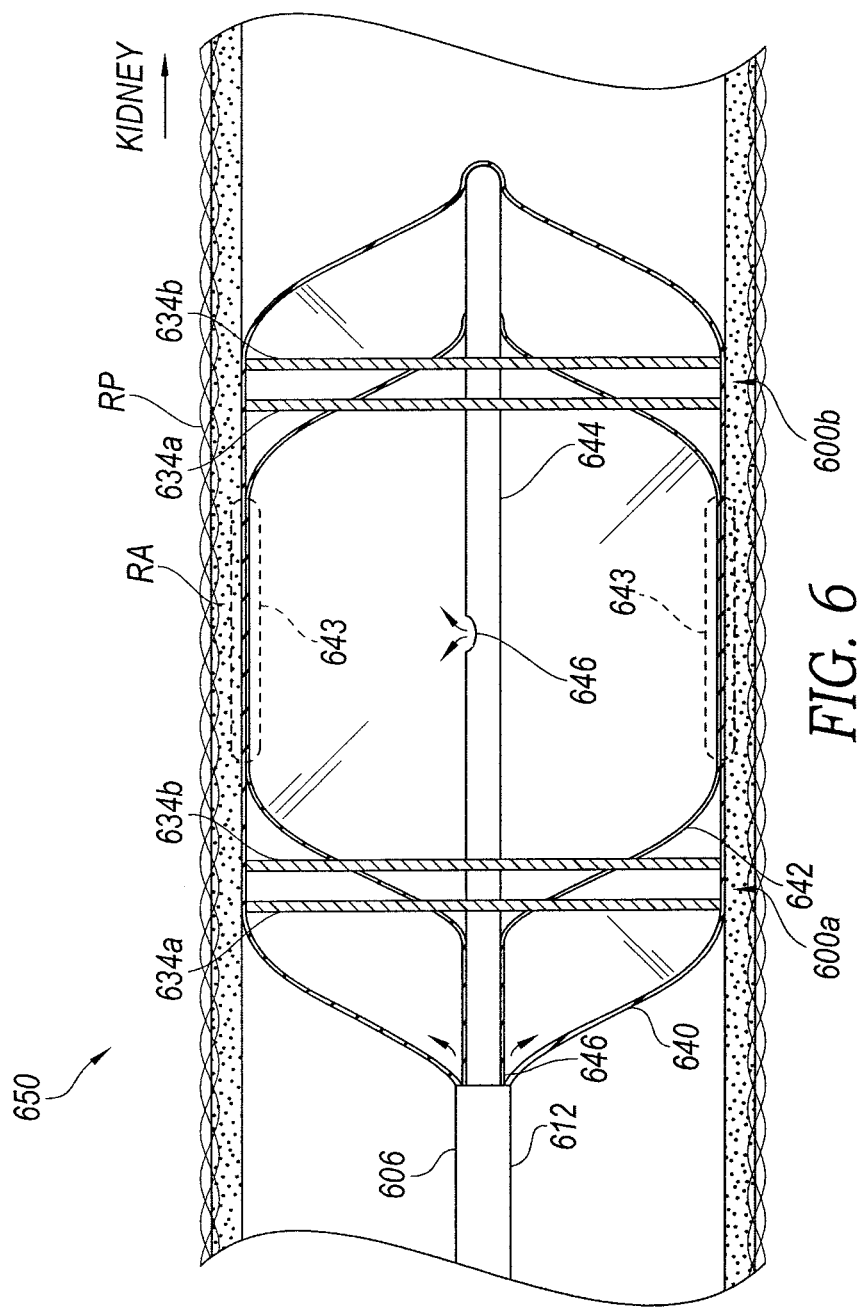
FIG. 6 is an enlarged side view of a distal portion of a treatment device within a renal artery in accordance with yet another embodiment of the present technology.

FIG. 6 is an enlarged side view of a distal portion of a treatment device 650 within a renal artery RA in accordance with yet another embodiment of the present technology. The treatment device 650 includes a number of features generally similar to the features of the treatment devices described above with reference to FIGS. 3B, 4B, 4C and 5. For example, the treatment device 650 includes an array of electrodes (identified individually as a first electrode array 600a and a second electrode array 600b, and referred to collectively as electrode arrays 600) proximal and distal to a neuromodulation area 643 (shown in broken lines). In the embodiment illustrated in FIG. 6, the treatment device 650 has a double balloon configuration in which a first inflatable body or outer balloon 640 is disposed over a second inflatable body or inner balloon 642. The inner balloon 642 can be configured to deliver therapeutic neuromodulation to nerves proximate a treatment site (e.g., the renal artery RA). For example, the inner balloon 642 can define an expansion chamber in which a cryogenic agent (e.g., nitrous oxide ($N_2O$)) can expand to provide therapeutically-effective cooling to tissue adjacent to the inflated inner balloon 642 (e.g., in the neuromodulation area 643). In other embodiments, the inner balloon 642 can be configured to provide therapeutic neuromodulation using other suitable means known in the art such as ultrasound (e.g., HIFU). In further embodiments, the inner balloon 642 may be omitted, and energy deliver elements (e.g., electrodes) can be disposed on an outer surface of the outer balloon 640 to deliver RF ablation energy and/or other forms of energy for neuromodulation.

As shown in FIG. 6, a proximal end portion of the outer balloon 640 can be coupled to a distal portion 612 of an outer shaft 606 and a proximal end portion of the inner balloon 642 can be coupled to an inner shaft 644 that extends through the outer shaft 606. In the illustrated embodiment, the inner shaft 644 extends through the outer and inner balloons 640 and 642 such that the distal end portions of the outer and inner balloons 640 and 642 can connect thereto, and therefore the inner shaft 644 can provide longitudinal support along the balloons 640 and 642. In other embodiments, the inner shaft 644 can extend partially into the balloons 640 and 642 or terminate proximate to the distal end of the outer shaft 606. The outer and inner shafts 606 and 644 can define or include supply lumens fluidly coupled at proximal end portions to one or more fluid sources and fluidly coupled at distal end portions to the outer and inner balloons 640 and 642. For example, the inner shaft 644 can include one or more openings 646 through which fluids (e.g., refrigerants or other cryogenic agents) can be delivered to the inner balloon 642 (e.g., as indicated by the arrows) to inflate or expand the inner balloon 642. Fluids (e.g., saline or air) can be delivered to the outer balloon 640 through a space or opening 646 between the outer and inner shafts 606 and 644 (e.g., as indicated by the arrows) and/or by a supply lumen spaced therebetween to inflate or expand the outer balloon 640.

The inner balloon 642 can have smaller dimensions than the outer balloon 640 such that the outer balloon 640 expands into full circumferential contact with the vessel wall along a length of the vessel and the inner balloon 642 expands to press against or otherwise contact a segment of the inner wall of the outer balloon 640. In the embodiment illustrated in FIG. 6, for example, the outer and inner balloons 640 and 642 contact each other at an interface extending around a full circumference of the inner balloon 642 spaced laterally inward of the electrode arrays 600. The portion of the outer balloon 640 in contact with the inflated inner balloon 642 can deliver therapeutically-effective neuromodulation (e.g., via cryotherapeutic cooling) to nerves proximate the adjacent vessel wall. Accordingly, the double balloon arrangement shown in FIG. 6 can deliver fully-circumferential neuromodulation. Non-targeted tissue proximal and distal to the contacting balloon walls is shielded or protected from neuromodulation by an inflation medium (e.g., saline solution, air, etc.) within the outer balloon 640, which may effectively act as insulation.

The outer and inner balloons 640 and 642 can be made from various compliant, non-compliant, and semi-compliant balloons materials. The outer balloon 640, for example, can be made from a compliant balloon material (e.g., polyurethane or silicone) such that when the outer balloon 640 is inflated, it can press against the inner wall of a vessel to provide stable contact therebetween. The inner balloon 642 can be made from semi-compliant and or non-compliant materials (e.g., formed from polyether block amide, nylon, etc.) to define a smaller expanded size. In other embodiments, the outer and inner balloons 640 and 642 can be made from other suitable balloon materials.

As shown in FIG. 6, the first electrode array 600a and the second electrode array 600b may be located at the outer wall of the outer balloon 640 and positioned proximal and distal to the neuromodulation area 643 (i.e., the region of the outer balloon 640 that contacts the inflated inner balloon 642). Each electrode array 600 can include a first conductive portion 634a and a second conductive portion 634b (referred to collectively as conductive portions 634) that extend around the circumference of the outer balloon 640 to define first and second electrode loops. In other embodiments, one or both of the electrode arrays 600 can include a single conductive portion or strip extending around the circumference of the outer balloon 640. The conductive portions 634 can be made from a conductive ink printed on the outer wall of the outer balloon 640 and/or other conductive materials that can attach to the outer balloon 640. In operation, the first electrode array 600a can stimulate nerves proximal to the neuromodulation area 643 and the second electrode array 600b can sense the resultant stimulation, or vice versa. The first and second conductive portions 634 of each electrode array 600 can be configured to provide bipolar or monopolar stimulation and/or recording depending upon which mode provides the highest signal response. For example, the first electrode array 600a can include one electrode (e.g., one conductive strip 634) for monopolar stimulation and the second electrode array 600b can include two electrodes (e.g., two conductive strips 634) for bipolar recording. In other embodiments, however, the electrode arrays 600 may have other arrangements and/or include different features.

The treatment device 650 can provide nerve stimulation and recording before, during, and/or after neuromodulation. For example, the electrode assemblies 600 can stimulate nerves and record the resultant nerve activity before neuromodulation to provide a set point against which subsequent nerve monitoring can be compared. This information can also be used to determine the level of power or current that must be delivered to ablate the nerves since each patient typically has different base line levels nerve activity. Therefore, the electrode arrays 600 can also provide diagnostic nerve monitoring. During the neuromodulation procedure, the electrode arrays 600 can monitor the reduction of nerve signal strength to confirm the effectiveness of the neuromodulation. For example, the electrode assemblies 600 can continually monitor nerve activity during neuromodulation by interleaving stimulation pulses and recording periods. In other embodiments, nerve monitoring periods can be spaced between neuromodulation periods to determine whether the nerves have been sufficiently modulated or if subsequent neuromodulation cycles are necessary to provide the desired modulation.

Figure 7:
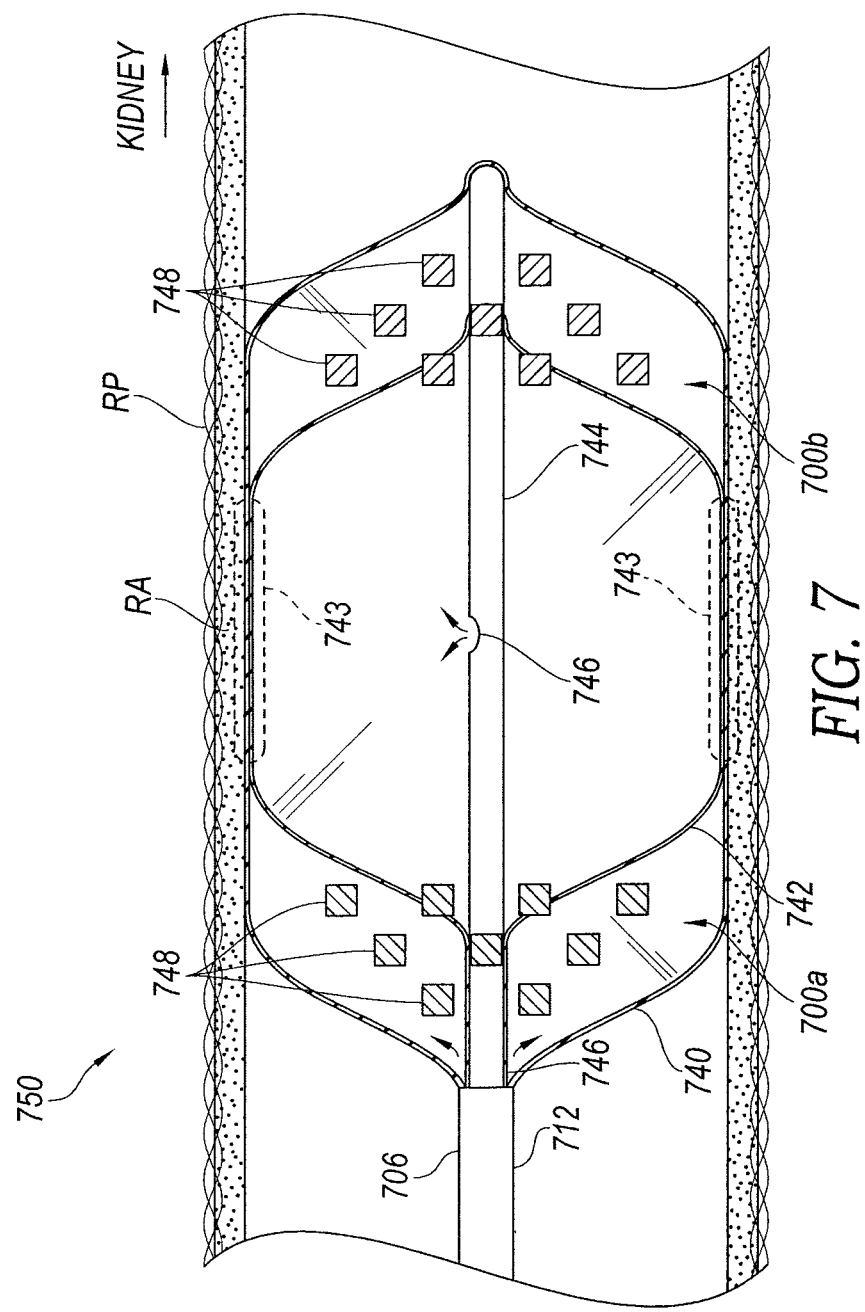
FIG. 7 is an enlarged side view of a distal portion of a treatment device within a renal artery in accordance with a further embodiment of the present technology.

FIG. 7 is an enlarged side view of a distal portion of a treatment device 750 within a renal artery RA in accordance with a further embodiment of the present technology. The treatment device 750 includes a number of features generally similar to the features of the treatment device 650 described above with reference to FIG. 6. For example, the treatment assembly 750 includes an outer balloon 740 in fluid communication with a first supply lumen via an opening 746 at a distal portion 712 of an outer shaft 706, and an inner balloon 742 in fluid communication with a second supply lumen via an opening 746 of an inner shaft 744. The outer balloon 740 can be inflated with a non-therapeutically effective fluid (e.g., air) to press against and maintain contact with the inner vessel wall. The inner balloon 742 can be inflated with a cryogenic agent (e.g., a refrigerant) and/or other fluid to contact a portion of the outer balloon 740 and provide neuromodulation (e.g., via cryotherapeutic cooling or ultrasound) about the full circumference of an adjacent vessel wall (e.g., within a neuromodulation region 743).

The treatment device 750 also includes first and second electrode arrays 700a and 700b (referred to collectively as electrode arrays 700) proximal and distal to the portion at which the inner balloon 742 contacts the outer balloon 740. Rather than continuous conductive strips around the circumference of the outer balloon 740, however, the electrode arrays 700 illustrated in FIG. 7 include a plurality of point electrodes 748 on or in an outer wall of the outer balloon 740. The point electrodes 748, for example, can be made from conductive ink printed on the outer balloon 740, conductive pads adhered to the outer balloon 740, and/or other suitable conductive features. The individual point electrodes 748 can be oriented about the circumference of the outer balloon 740 in various different patterns and provide monopolar and/or bipolar nerve stimulation and recording before, during and/or after neuromodulation.

Figure 8:
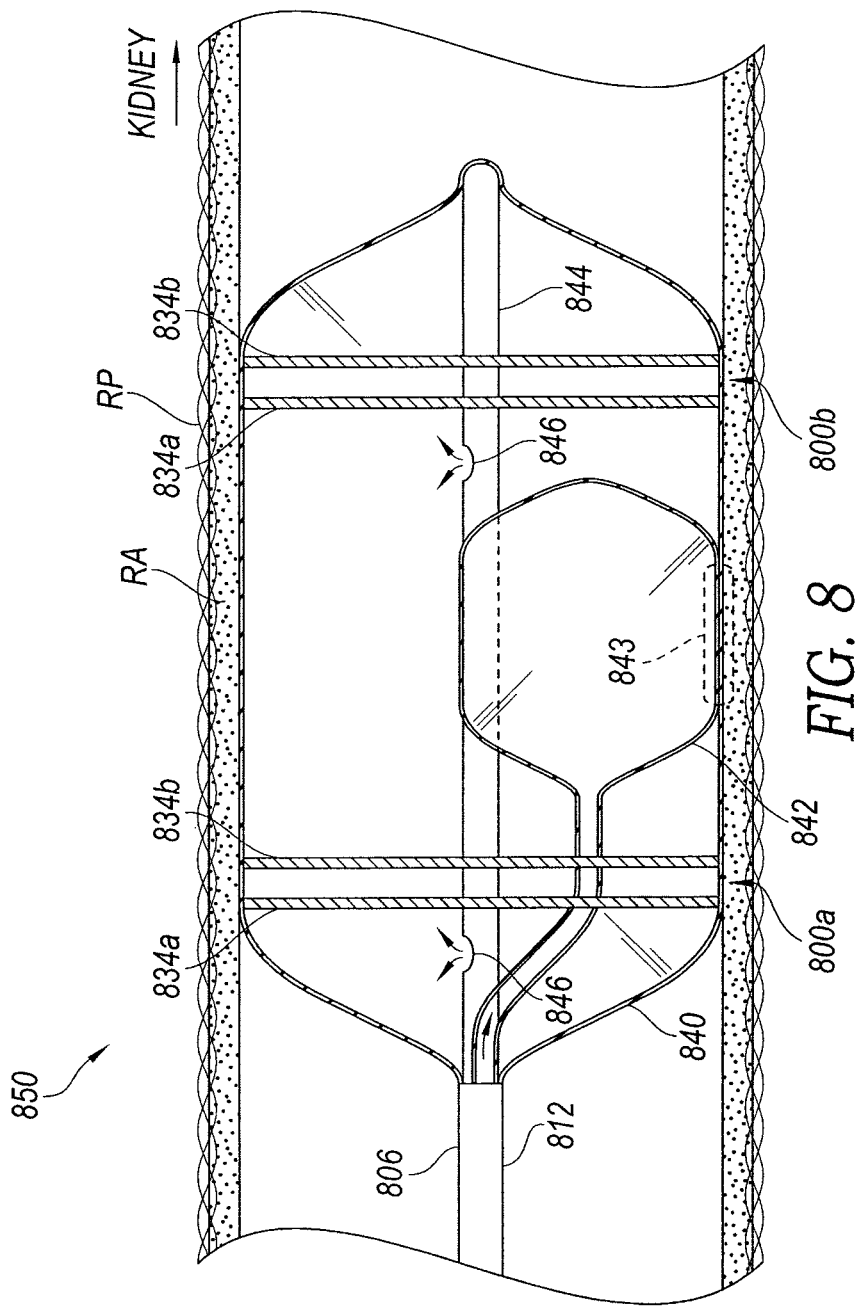
FIG. 8 is an enlarged side view of a distal portion of a treatment device within a renal artery in accordance with an additional embodiment of the present technology.

FIG. 8 is an enlarged side view of a distal portion of a treatment device 850 within a renal artery RA in accordance with an additional embodiment of the present technology. The treatment device 850 includes several features generally similar to the features of the treatment device 650 described above with reference to FIG. 6. For example, the treatment device 850 includes first and second electrode arrays 800a and 800b (referred to collectively as electrode arrays 800) on an outer balloon 840 and positioned proximal and distal to a neuromodulation region 843 provided by an inner balloon 842. In the embodiment illustrated in FIG. 8, the inner balloon 842 has a smaller outer diameter in an inflated state than that of the outer balloon 840 and is attached to an interior surface of the outer balloon 840 using an adhesive, a heat-bond and/or other types of balloon connection. The outer balloon 840 can be fluidly coupled to a supply lumen defined by a shaft 844 that delivers an insulative medium (e.g., a heated liquid, heated gas, ambient air, etc.) to the outer balloon 840 via openings 846, and the inner balloon 842 can be fluidly coupled to a separate supply lumen (not shown) that delivers an inflation fluid (e.g., a cryogenic agent) to the inner balloon 842.

In use, the outer balloon 840 expands into full circumferential contact with the vessel wall to provide tissue apposition for signal transfer to and from the vessel wall via the electrode arrays 800. The inner balloon 842 is essentially radially pulled toward only the portion of the vessel wall adjacent to where the inner balloon 842 is attached to the outer balloon 840. When a cryogenic agent and/or other therapeutic medium is introduced into the inner balloon 842, non-targeted tissue that is not adjacent to the inner balloon 842 is shielded or protected from ablation by the inflation medium located within the outer balloon 840. The targeted tissue adjacent to the inner balloon 842 is ablated, resulting in a partial circumferential neuromodulation. The inner balloon 842 can be shaped or otherwise configured to provide a non-continuous, helical, and/or other type of ablation pattern.

Figure 9A:
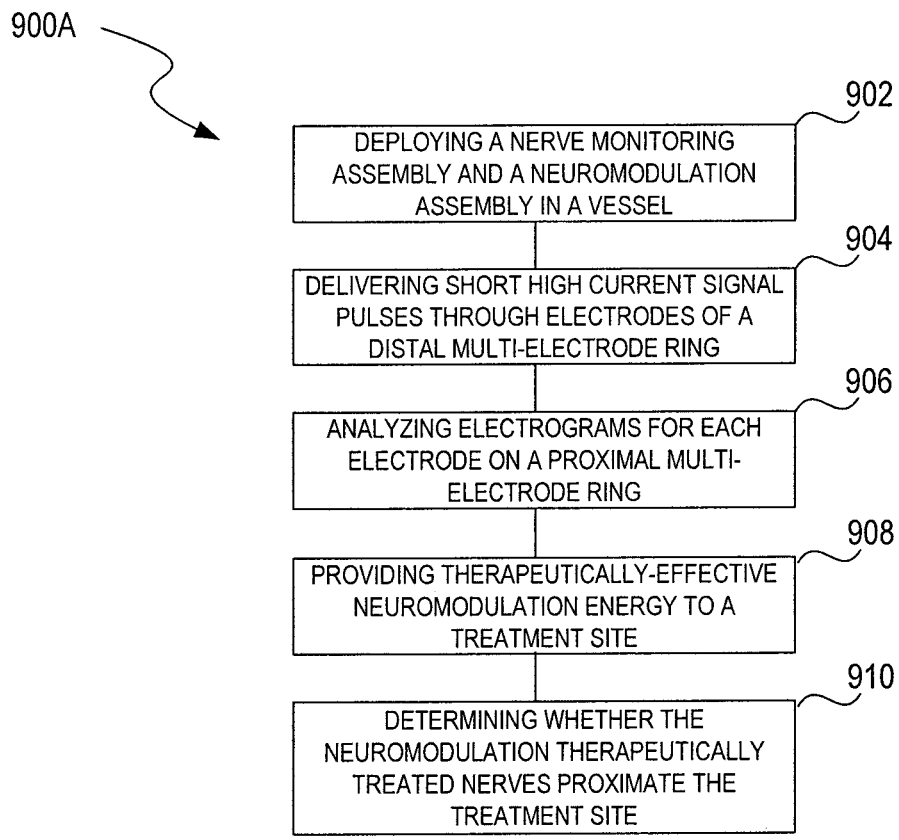
FIG. 9A is a block diagram illustrating a method of endovascularly monitoring nerve activity in accordance with an embodiment of the present technology.

FIG. 9A is a block diagram illustrating a method 900A of endovascularly monitoring nerve activity in accordance with an embodiment of the present technology. The method 900A can include deploying a nerve monitoring assembly and a neuromodulation assembly in a vessel (e.g., a renal artery; block 902). The nerve monitoring assembly can include a plurality of multi-electrode rings (e.g., similar to the multi-electrode loops 402 described above with reference to FIGS. 4A-4C) connected to a distal portion of a catheter shaft. The multi-electrode rings can be made of nitinol or other shape memory materials such that they can be deployed by simply moving the catheter shaft and a sheath covering the multi-electrode rings relative to one another (e.g., pulling the sheath proximally, pushing the catheter shaft distally, etc.). Each multi-electrode ring can include a plurality of electrodes spaced around the circumference of the ring and communicatively coupled to signal wires extending through the catheter shaft. The signal wires can extend outside the body where they are operably coupled to a signal generator and/or receiver (e.g., a NIM) to generate stimuli and record the resultant action potential of the proximate neural fibers.

When the neuromodulation assembly is deployed, at least one and often two or more multi-electrode rings ("distal rings") or another distal electrode assembly can be positioned distal to the neuromodulation assembly and at least one multi-electrode ring ("proximal ring") or other proximal electrode assembly can be positioned proximal to the neuromodulation assembly. In other embodiments, the nerve monitoring assembly can include one, two, or more multi-electrode rings on either side of the neuromodulation assembly. In further embodiments, other types of electrode arrays can be positioned proximal and distal to the neuromodulation assembly. The neuromodulation assembly, such as a single- or multi-electrode device or a cryoballoon, can be integrated with the same catheter shaft as the multi-electrode rings and positioned between the proximal and distal rings. In other embodiments, the neuromodulation assembly can be attached to a separate catheter shaft and deployed between proximal and distal multi-electrode rings.

The method 900A can further include delivering a plurality of short, high current stimulus pulses through the electrodes on one or both of the multi-electrode rings positioned distal to the neuromodulation assembly (block 904), and analyzing an electrogram of at least one of the electrodes on the proximal ring resulting from the stimulus pulse (block 906). For example, a signal generator can pass a current having a magnitude of about 10-60 mA (e.g., 20 mA, 50 mA, etc.) for a pulse length of about 25-1,500 μs (e.g., 100-400 μs, 1 ms, etc.) between the electrodes of the distal rings in the delivering process 904. The signal generator can also control the frequency of the signal such that the signal has a frequency of about 10-50 Hz (e.g., 20 Hz). After a predetermined time interval, a separate electrogram can be recorded through at least one electrode on the proximal ring. For example, a separate electrogram can be recorded through each of the electrodes of the proximal electrode ring. The length of the time interval between stimulation and recording depends on the separation of the distal and proximal rings along the length of the vessel such that the proximal ring picks up the signal resulting from the induced stimulus. For example, the time interval can be about 10-50 ms for rings spaced 10-50 mm apart. In an alternative embodiment, the delivering process (block 904) of the method 900A can include delivering the short, high current stimulus pulses through at least one of the proximal electrode rings (e.g., proximal electrode assembly), and the analyzing process (block 906) of the method 900A can include analyzing an electrogram of at least one of the electrodes of the distal electrode rings (e.g., distal electrode assembly).

The method 900A can further include providing therapeutically-effective neuromodulation energy (e.g., cryogenic cooling, RF energy, ultrasound energy, etc.) to a target site using the neuromodulation assembly (block 908). After providing the therapeutically-effective neuromodulation energy (block 908), the method 900A includes determining whether the neuromodulation therapeutically treated or otherwise sufficiently modulated nerves or other neural structures proximate the treatment site (block 910). For example, the process of determining whether the neuromodulation therapeutically treated the nerves can include determining whether nerves were sufficiently denervated or otherwise disrupted to reduce, suppress, inhibit, block or otherwise affect the afferent and/or efferent renal signals.

Figure 9B:
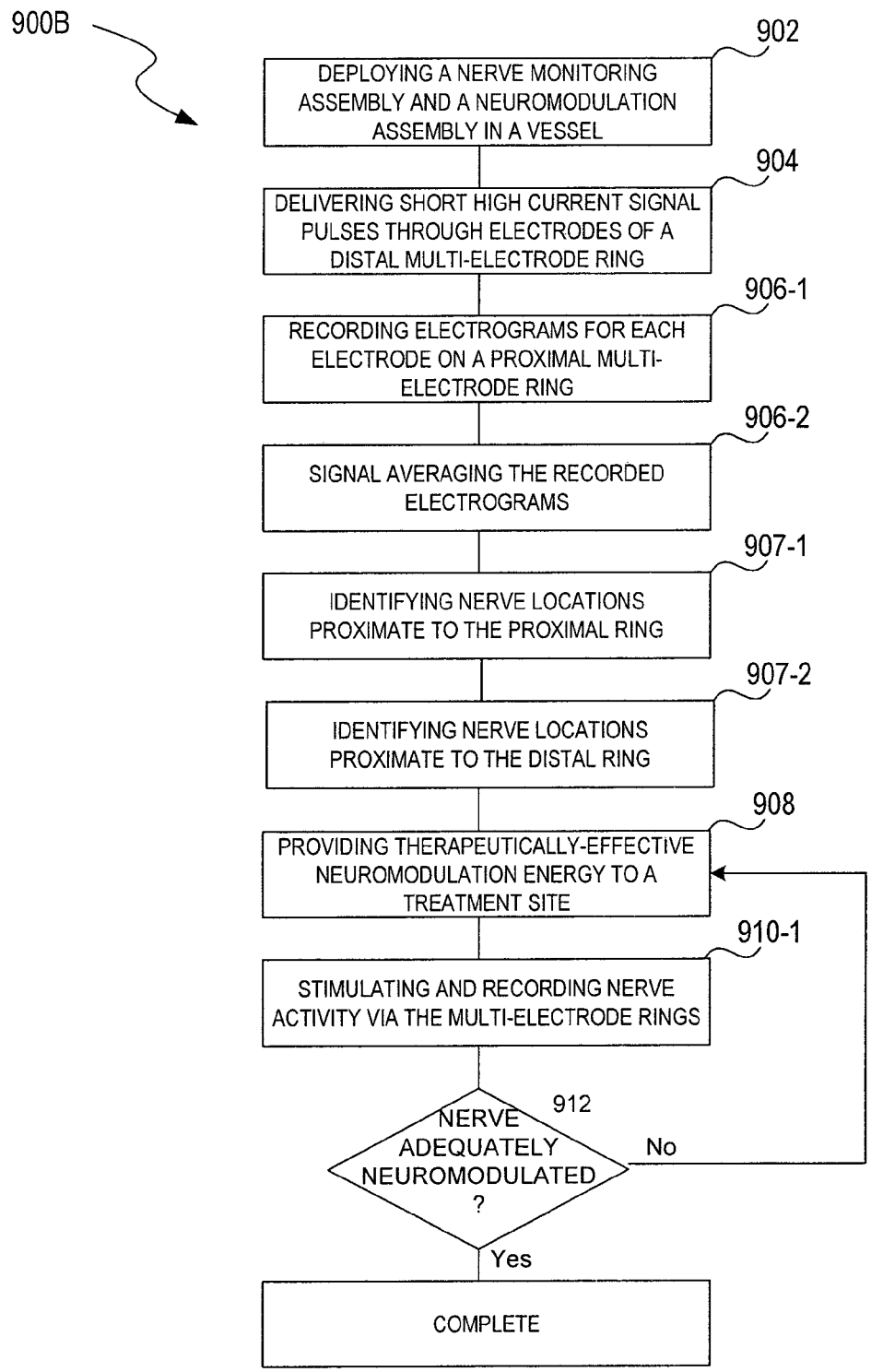
FIG. 9B is a block diagram illustrating a method of endovascularly monitoring nerve activity in accordance with another embodiment of the present technology.

FIG. 9B is a block diagram illustrating a method 900B of endovascularly monitoring nerve activity in accordance with an embodiment of the present technology. The method 900B can include deploying a nerve monitoring assembly and a neuromodulation assembly in a vessel (block 902) and delivering short, high current signal pulses through an electrode assembly (block 904) as described above with respect to the method 900A in FIG. 9A. In this embodiment, the analyzing process (block 906 of FIG. 9A) can optionally include recording the electrograms for each electrode on the proximal electrode ring or other proximal electrode assembly (block 906-1) and signal averaging a plurality of the recorded electrode signals (e.g., 10-100 recorded electrode signals) resulting from a corresponding plurality of stimulus pulses to enhance the recorded signal (block 906-2).

The method 900B can optionally include identifying the nerve location proximate one or more of the electrode rings. For example, one or more of the recorded electrode signals may include a deflection or other change in the recorded current indicating an action potential caused by the stimulus (e.g., identified via signal averaging) indicating the transmission of an electrical impulse from the stimulus pulse via adjacent nerves. Electrode signals that include changes in current intensity correspond with the electrodes on the proximal ring positioned proximate to nerves. The higher the deflection or change in current intensity, the closer the electrode is to the nerves. This information can be used to identify electrodes on the proximal ring close to the nerves for effective nerve stimulation or recording (block 907-1). Optionally, the method 900 can include stimulating nerves via the proximal ring and recording electrograms of the individual electrodes at one of the distal rings to determine the location of nerves proximate the distal rings (block 907-2).

The method 900B can also include providing therapeutically-effective neuromodulation energy (e.g., cryogenic cooling, RF energy, ultrasound energy, etc.) to a target site using the neuromodulation assembly (block 908). In this embodiment, the process of determining whether the neuromodulation treated the nerves proximate the target site (block 910 in FIG. 9A) can include repeating the nerve stimulation (block 904) and analyzing processes (block 906) discussed above to assess whether the neuromodulation caused any changes in the nerve activity (block 910-1). For example, short, high current stimulus pulses can be transmitted via the proximal or distal rings and the resultant nerve activity can be recorded by the opposing ring(s). The method 900B can then determine whether the nerves have been adequately modulated (block 912). For example, if the current density or other parameter observed in the recording electrodes proximate the nerve locations is below a threshold value, then the neuromodulation step may have effectively modulated or stopped conduction of the adjacent nerves and the neuromodulation process can be complete. On the other hand, if nerve activity is detected above a threshold value, the process of neuromodulating (block 908) and monitoring the resultant nerve activity (block 910-1) can be repeated until the nerves have been effectively modulated.

In various embodiments, the methods 900A and 900B can also include repeating the nerve monitoring and neuromodulation steps in the opposite direction to confirm that the nerves have been adequately modulated. The methods 900A and 900B can also optionally be repeated after a time period (e.g., 5-30 minutes, 2 hours, 1 day, etc.) to confirm that the nerves were adequately ablated (e.g., rather than merely stunned) and have not resumed conduction.

In other embodiments, the methods 900A and 900B can be performed using other nerve monitoring assemblies or electrode arrays described above with reference to FIGS. 3A-8 and/or other suitable electrode arrangements. For example, the neuromodulation assembly can include multiple point electrodes spaced around the circumference of a balloon as described above with respect to FIG. 7. In other embodiments, continuous wire loop electrodes and/or conductive strips on balloons can be used to identify nerve location and monitor nerve activity.

IV. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 10:
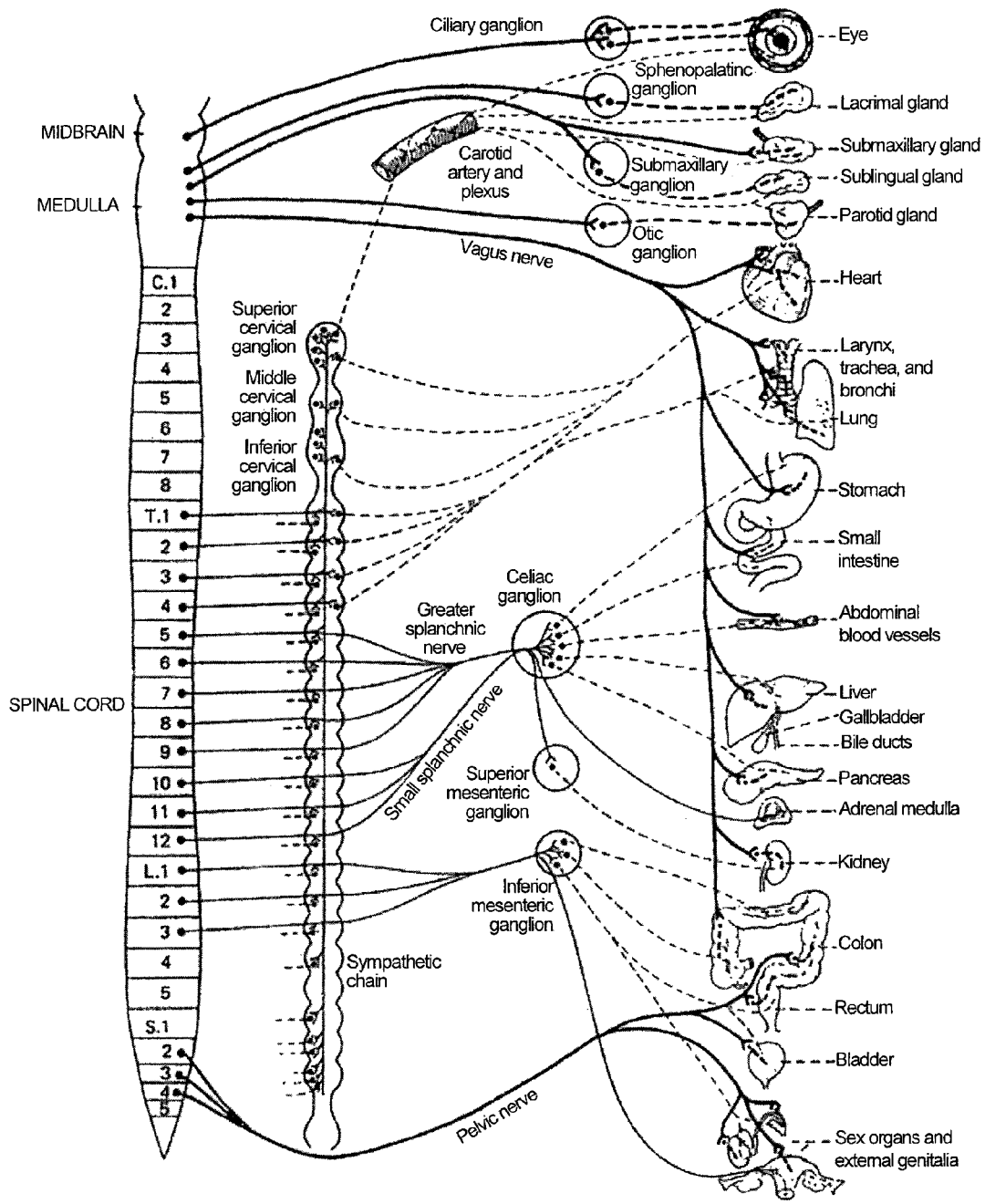
FIG. 10 is a conceptual illustration of the sympathetic nervous system (SNS) and how the brain communicates with the body via the SNS.

As shown in FIG. 10, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 11:
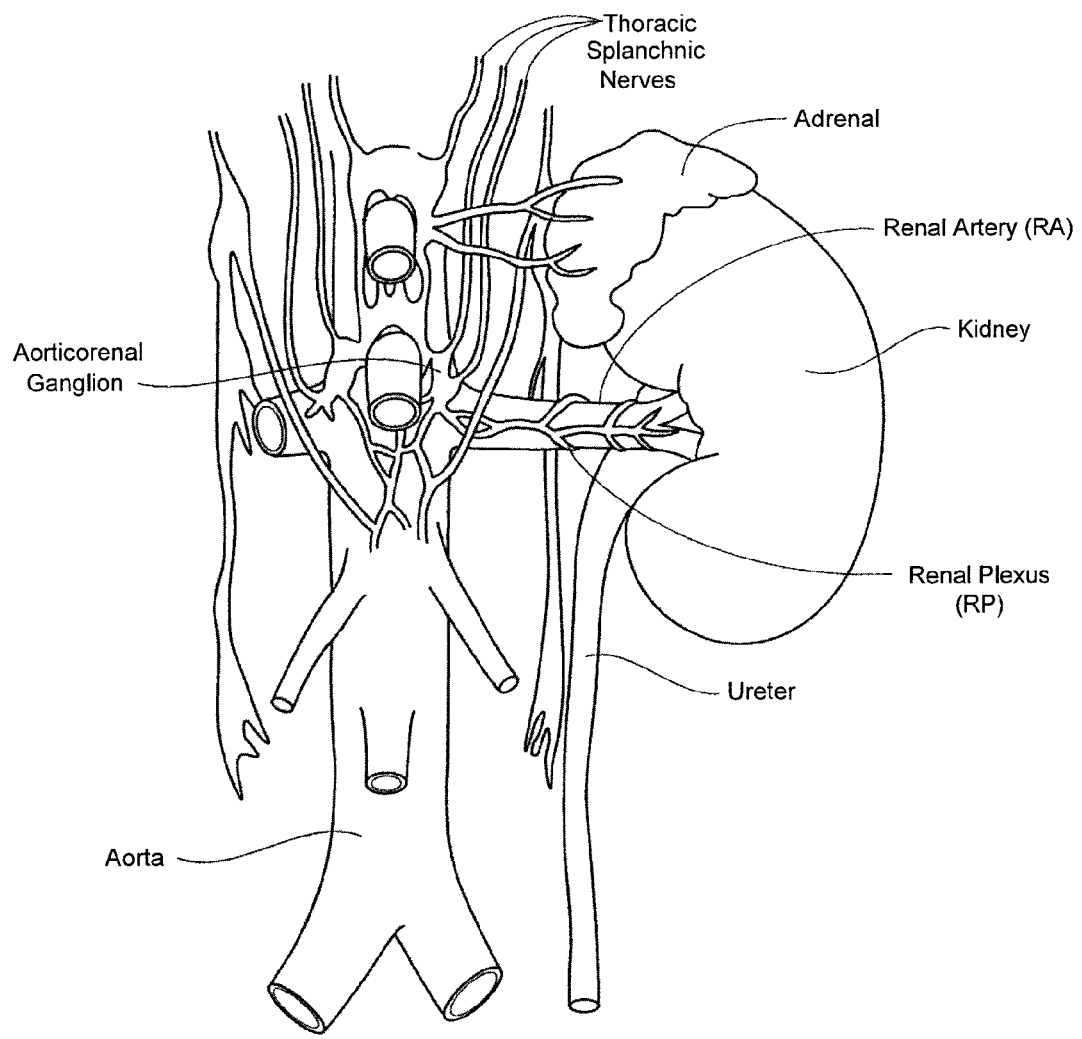
FIG. 11 is an enlarged anatomic view of nerves innervating a left kidney to form the renal plexus surrounding the left renal artery.

As shown in FIG. 11, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 12:
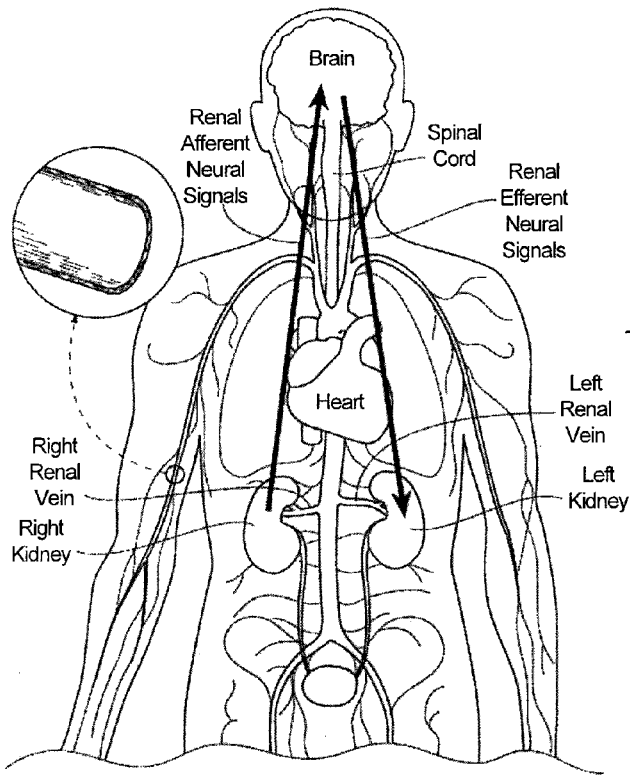
FIGS. 12 and 13 are anatomic and conceptual views of a human body, respectively, depicting neural efferent and afferent communication between the brain and kidneys.
Figure 13:
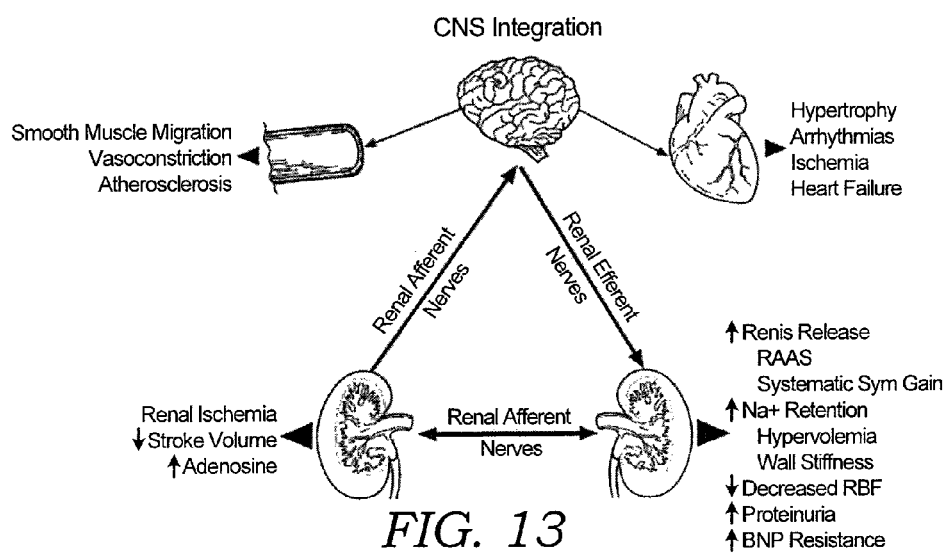

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 12 and 13, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 10. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 14:
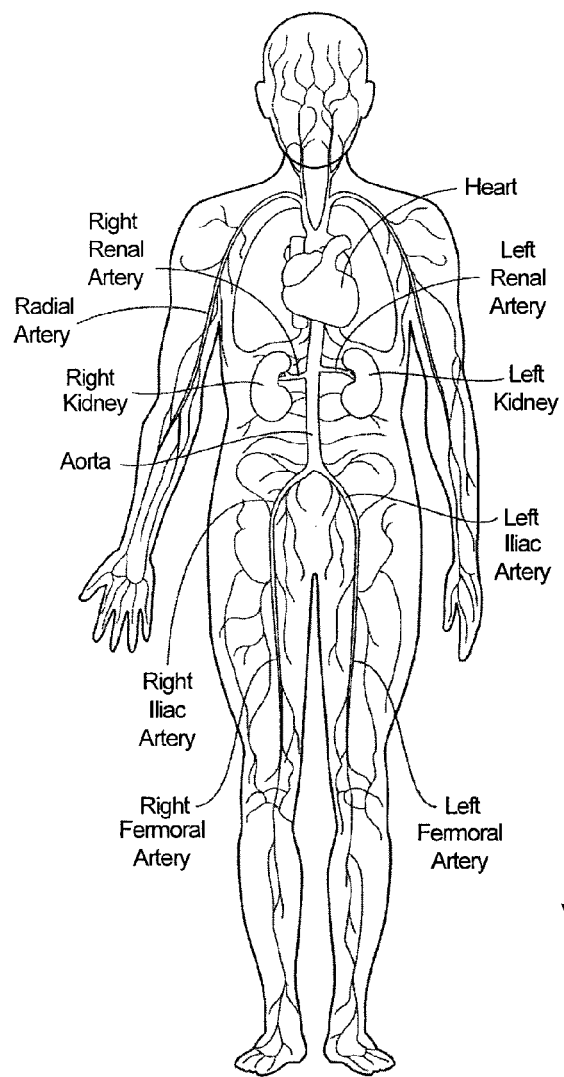
FIGS. 14 and 15 are anatomic views illustrating, respectively, an arterial vasculature and a venous vasculature of a human.

In accordance with the present technology, neuromodulation of a left and/or right renal plexus RP, which is intimately associated with a left and/or right renal artery, may be achieved through intravascular access. As FIG. 14 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 15:
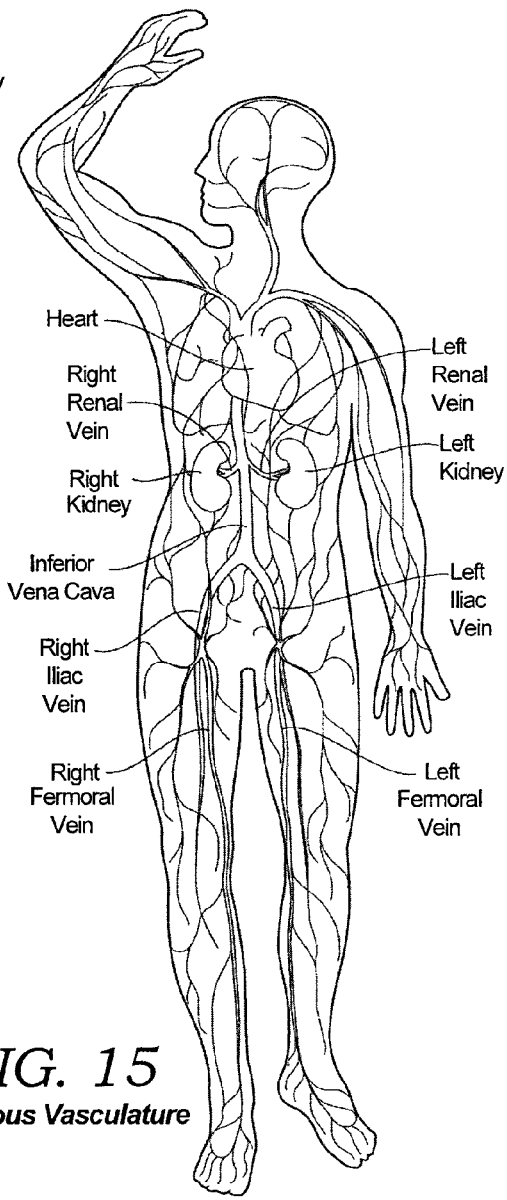

As FIG. 15 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the neuromodulation structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

V. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of monitoring renal nerve activity, the method comprising:
deploying a nerve monitoring assembly in a renal artery of a human patient, wherein the nerve monitoring assembly comprises a first electrode array at a distal portion of a shaft and a second electrode array spaced laterally apart from the first electrode array, wherein deploying the nerve monitoring assembly in the renal artery further comprises inflating a first balloon within the renal artery, wherein the inflated first balloon contacts an inner wall of the renal artery, and wherein the first and second electrode arrays are on an outer surface of the first balloon;

delivering a neuromodulation assembly to a target site within the renal artery between the first and second electrode arrays, wherein delivering the neuromodulation assembly to the target site within the renal artery between the first and second electrode arrays further comprises inflating a second balloon within the first balloon, wherein the second balloon is configured to contact the first balloon to define a neuromodulation region;

stimulating renal nerves with the first electrode array, wherein the stimulation energy is at a magnitude which induces renal nerve activity;

recording, with the second electrode array, renal nerve activity resulting from the stimulating act; and applying therapeutically-effective neuromodulation energy to the target site with the neuromodulation assembly, wherein the neuromodulation energy is at a level which inhibits, reduces, or blocks renal nerves, and wherein applying therapeutically-effective neuromodulation energy to the target site with the neuromodulation assembly further comprises applying cryogenic cooling to the renal artery proximate the neuromodulation region.

2. The method of claim 1 wherein:

stimulating renal nerves with the first electrode array comprises delivering a plurality of stimulus pulses with the first electrode array, each stimulus pulse having an intensity of about 20-60 mA at a pulse length of about 100-400 μs;

recording renal nerve activity with the second electrode array comprises recording electrograms of individual electrodes of the second electrode array, wherein the electrograms correspond to the nerve activity resulting from the stimulus pulses; and wherein the method further comprises detecting nerve locations proximate the second electrode array, wherein the second electrode array is proximal to the first electrode array.

3. The method of claim 1 wherein stimulating renal nerves with the first electrode array comprises delivering a current pulse having an intensity of at least 20 mA.

4. The method of claim 1 wherein deploying the nerve monitoring assembly in the renal artery comprises deploying the first electrode array proximal to the second electrode array.

5. The method of claim 1 wherein:

stimulating renal nerves and recording the resultant nerve activity is performed after applying a first cycle of therapeutically-effective neuromodulation energy to the target site; and the method further comprises applying a second cycle of therapeutically-effective neuromodulation energy to the target site with the neuromodulation assembly when the recorded nerve activity is above a predetermined threshold.

6. The method of claim 1 wherein the first electrode array is positioned at least 15 mm apart from the second electrode array along an axis of the renal artery.

7. The method of claim 1 wherein the first electrode array is positioned 10-20 mm apart from the second electrode array along an axis of the renal artery.

8. The method of claim 1 wherein the nerve monitoring assembly and the neuromodulation assembly are sequentially delivered to the target site.

9. The method of claim 8 wherein the nerve monitoring assembly is deployed at the target site before the application of neuromodulation energy.

10. The method of claim 8 wherein the nerve monitoring assembly is deployed at the target site after the application of neuromodulation energy.

* * * * *